United States Patent
Lund

(10) Patent No.: US 11,497,484 B2
(45) Date of Patent: Nov. 15, 2022

(54) KNOTLESS SELF-LOCKING ANCHOR CONSTRUCTS AND METHODS OF TISSUE FIXATION

(71) Applicant: Arthrex, Inc., Naples, FL (US)

(72) Inventor: Jereme J. Lund, Ingleside, IL (US)

(73) Assignee: Arthrex, Inc., Naples, FL (US)

( * ) Notice: Subject to any disclaimer, the term of this patent is extended or adjusted under 35 U.S.C. 154(b) by 556 days.

(21) Appl. No.: 16/749,303

(22) Filed: Jan. 22, 2020

(65) Prior Publication Data

US 2020/0155141 A1  May 21, 2020

Related U.S. Application Data

(63) Continuation of application No. 15/883,771, filed on Jan. 30, 2018, now Pat. No. 10,575,842.

(60) Provisional application No. 62/614,748, filed on Jan. 8, 2018, provisional application No. 62/481,055, filed on Apr. 3, 2017, provisional application No. 62/459,353, filed on Feb. 15, 2017, provisional application No. 62/457,099, filed on Feb. 9, 2017.

(51) Int. Cl.

| A61B 17/04 | (2006.01) |
|---|---|
| A61L 31/04 | (2006.01) |
| A61B 17/00 | (2006.01) |
| A61B 17/06 | (2006.01) |

(52) U.S. Cl.
CPC ........ *A61B 17/0401* (2013.01); *A61L 31/048* (2013.01); *A61B 17/0466* (2013.01); *A61B 17/06066* (2013.01); *A61B 2017/00477* (2013.01); *A61B 2017/00867* (2013.01); *A61B 2017/0403* (2013.01); *A61B 2017/0404* (2013.01); *A61B 2017/044* (2013.01); *A61B 2017/0409* (2013.01); *A61B 2017/0412* (2013.01); *A61B 2017/0414* (2013.01); *A61B 2017/0445* (2013.01); *A61B 2017/0448* (2013.01); *A61B 2017/0458* (2013.01); *A61B 2017/0464* (2013.01); *A61B 2017/0477* (2013.01)

(58) Field of Classification Search
CPC ............ A61B 17/0401; A61B 17/0466; A61B 2017/00867; A61B 2017/0409; A61B 2017/0464

See application file for complete search history.

(56) References Cited

U.S. PATENT DOCUMENTS

| 4,187,558 A | 2/1980 | Dahlen et al. |
|---|---|---|
| 4,301,551 A | 11/1981 | Dore et al. |
| 4,776,851 A | 10/1988 | Bruchman et al. |
| 4,790,850 A | 12/1988 | Dunn et al. |
| 4,792,336 A | 12/1988 | Hlavacek et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,129,902 A | 7/1992 | Goble et al. |

(Continued)

*Primary Examiner* — Phong Son H Dang

(57) ABSTRACT

Systems and methods for soft tissue to bone repairs, without knot tying. The soft tissue repair systems include self-cinching constructs with a fixation device, a flexible coupler and an optional shuttle/pull device attached to the flexible strand. An accordion-style weave region is formed by pulling on the shuttle/pull device subsequent to the fixation device being secured into the bone, to allow desired tensioning of soft tissue to be fixated or repaired relative to the bone and secured self-locking of the construct.

13 Claims, 19 Drawing Sheets

(56) References Cited

U.S. PATENT DOCUMENTS

| | | |
|---|---|---|
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,562,669 A | 10/1996 | McGuire |
| 5,575,819 A | 11/1996 | Amis |
| 5,628,756 A | 5/1997 | Barker, Jr. et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck, Jr. et al. |
| 5,964,764 A | 10/1999 | West, Jr. et al. |
| 6,296,659 B1 | 10/2001 | Foerster |
| 6,517,578 B2 | 2/2003 | Hein |
| 6,533,802 B2 | 3/2003 | Bojarski et al. |
| 7,097,654 B1 | 8/2006 | Freedland |
| 7,494,506 B2 | 2/2009 | Brulez et al. |
| 7,601,165 B2 | 10/2009 | Stone |
| 7,658,751 B2 | 2/2010 | Stone et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,857,830 B2 | 12/2010 | Stone et al. |
| 7,875,058 B2 | 1/2011 | Holmes, Jr. |
| 7,905,903 B2 | 3/2011 | Stone et al. |
| 7,909,851 B2 | 3/2011 | Stone et al. |
| 7,914,539 B2 | 3/2011 | Stone et al. |
| 7,959,650 B2 | 6/2011 | Kaiser et al. |
| 7,981,139 B2 | 7/2011 | Martin et al. |
| 8,088,130 B2 | 1/2012 | Kaiser et al. |
| 8,109,965 B2 | 2/2012 | Stone et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 8,273,106 B2 | 9/2012 | Stone et al. |
| 8,298,262 B2 | 10/2012 | Stone et al. |
| 8,303,604 B2 | 11/2012 | Stone et al. |
| 8,361,113 B2 | 1/2013 | Stone et al. |
| 8,460,379 B2 | 6/2013 | Albertorio et al. |
| 8,562,645 B2 | 10/2013 | Stone et al. |
| 8,562,647 B2 | 10/2013 | Kaiser et al. |
| 8,628,573 B2 | 1/2014 | Roller et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,840,645 B2 | 9/2014 | Denham et al. |
| 8,926,662 B2 | 1/2015 | Perriello et al. |
| 8,936,621 B2 | 1/2015 | Denham et al. |
| 8,951,286 B2 | 2/2015 | Sugimoto et al. |
| 9,017,381 B2 | 4/2015 | Kaiser et al. |
| 9,078,644 B2 | 7/2015 | Stone |
| 9,107,653 B2 | 8/2015 | Sullivan |
| 9,149,267 B2 | 10/2015 | Norton et al. |
| 9,179,950 B2 | 11/2015 | Zajac et al. |
| 9,314,241 B2 | 4/2016 | Stone et al. |
| 9,332,979 B2 | 5/2016 | Sullivan et al. |
| 9,357,992 B2 | 6/2016 | Stone et al. |
| 9,370,350 B2 | 6/2016 | Norton |
| 9,421,008 B2 | 8/2016 | Burkhart et al. |
| 9,445,803 B2 | 9/2016 | Marchand et al. |
| 9,463,013 B2 | 10/2016 | Pilgeram et al. |
| 9,486,211 B2 | 11/2016 | Stone et al. |
| 9,492,158 B2 | 11/2016 | Stone et al. |
| 9,498,204 B2 | 11/2016 | Denham et al. |
| 9,504,462 B2 | 11/2016 | Dooney et al. |
| 9,532,777 B2 | 1/2017 | Kaiser et al. |
| 9,539,003 B2 | 1/2017 | Stone et al. |
| 9,572,655 B2 | 2/2017 | Denham et al. |
| 9,603,591 B2 | 3/2017 | Denham et al. |
| 9,615,821 B2 | 4/2017 | Sullivan |
| 9,974,534 B2 | 5/2018 | Troxel et al. |
| 10,004,493 B2 | 6/2018 | Stone et al. |
| 10,070,856 B1 | 9/2018 | Black et al. |
| 10,092,288 B2 | 10/2018 | Denham et al. |
| 10,265,060 B2 | 4/2019 | Dooney et al. |
| 10,368,855 B2 | 8/2019 | Burkhart |
| 10,398,426 B2 | 9/2019 | Burkhart et al. |
| 10,610,217 B2 | 4/2020 | Stone et al. |
| 2007/0010857 A1 | 1/2007 | Sugimoto et al. |
| 2007/0185532 A1 | 8/2007 | Stone et al. |
| 2009/0076547 A1 | 3/2009 | Sugimoto et al. |
| 2011/0208239 A1 | 8/2011 | Stone et al. |
| 2011/0270278 A1 | 11/2011 | Overes et al. |
| 2012/0109194 A1 | 5/2012 | Miller et al. |
| 2012/0197271 A1 | 8/2012 | Astorino et al. |
| 2012/0239085 A1 | 9/2012 | Schlotterback et al. |
| 2013/0096611 A1 | 4/2013 | Sullivan |
| 2013/0110165 A1 | 5/2013 | Burkhart et al. |
| 2013/0345750 A1 | 12/2013 | Sullivan |
| 2014/0052179 A1 | 2/2014 | Dreyfuss et al. |
| 2014/0249577 A1 | 9/2014 | Pilgeram |
| 2015/0141995 A1 | 5/2015 | Norton |
| 2016/0007989 A1 | 1/2016 | Overes et al. |
| 2017/0035412 A1 | 2/2017 | Dooney et al. |
| 2017/0049434 A1 | 2/2017 | Dooney et al. |
| 2017/0105716 A1 | 4/2017 | Burkhart |
| 2017/0311947 A1 | 11/2017 | Kaiser et al. |
| 2018/0296207 A1 | 10/2018 | Burkhart et al. |

KNOTLESS SELF-LOCKING ANCHOR CONSTRUCTS AND METHODS OF TISSUE FIXATION

CROSS-REFERENCE TO RELATED APPLICATIONS

This application is a continuation of U.S. application Ser. No. 15/883,771, filed Jan. 30, 2018, the disclosures of which is incorporated by reference in its entirety herein. This application also claims the benefit of U.S. Provisional Application No. 62/457,099 filed Feb. 9, 2017; U.S. Provisional Application No. 62/459,353, filed Feb. 15, 2017; U.S. Provisional Application No. 62/481,055, filed Apr. 3, 2017; and U.S. Provisional Application No. 62/614,748, filed Jan. 8, 2018, the disclosures of all of which are incorporated by reference in their entireties herein.

BACKGROUND

The disclosure relates to surgical devices and, more specifically, to knotless self-locking anchor constructs and associated methods of tissue repairs.

SUMMARY

Knotless self-locking constructs, surgical systems and assemblies, and methods of tissue repairs are disclosed. A self-locking anchor can create a knotless, self-locking repair. A soft tissue repair system includes a self-cinching construct with a fixation device, a flexible coupler and a shuttle/pull device attached to the flexible coupler and provided within the body of the fixation device. An accordion-style weave region is formed by pulling on the shuttle/pull device subsequent to the fixation device being secured into the bone. A flexible coupler may be tape such as suture tape.

Methods of self-locking tissue repairs are also disclosed. A first tissue is approximated to a second tissue with a knotless self-locking surgical construct that includes a self-locking tensionable construct with a self-locking mechanism. A flexible coupler (tape) is passed multiple times through itself within a body of a fixation device, to create a construct that is tensionable after insertion in bone (to allow attached tissue to be brought proximate to bone) and does not require tying of any knots.

A soft tissue repair system includes a self-cinching construct with a fixation device, a flexible coupler with two flexible ends, and an eyelet attached to the flexible coupler and secured to the body of the fixation device. An accordion-style weave region is formed by passing one of the flexible ends through the flexible coupler multiple times. Subsequent to the formation of the accordion-style weave region, the two flexible ends are joined/brought together to form a single end to facilitate passing through tissue. Once the single end has been passed through or around tissue, the single end is cut to form again two flexible free ends. One of the ends is anchored and the other end may be pulled to tension and lock the construct. A flexible coupler may be suture or suture tape.

A soft tissue repair system includes a plurality of flexible couplers, for example, two flexible couplers with two accordion-style weave regions and four flexible free ends. All four ends may be connected (brought together) in any combination, for example, all ends may be spliced together to form a single spliced end. Once the spliced end has been passed through or around tissue, the spliced end is cut to form again four flexible free ends. The two ends of each flexible coupler may then be employed to secure a first tissue to a second tissue, for example, in a SpeedBridge technique. The two flexible couplers may be similar or dissimilar.

Methods of self-locking tissue repairs are also disclosed. A first tissue is approximated to a second tissue with a knotless self-locking surgical construct that includes at least one self-locking tensionable construct with a self-locking mechanism. At least one flexible coupler (suture or tape) with two free ends is passed through a body of a fixation device and attached to a flexible eyelet of the fixation device. One of the free ends is passed multiple times through the flexible coupler to form an accordion-style weave region. The two ends are then joined/brought together to form a single end to facilitate passing through tissue. Once the single end has been passed through or around tissue, the single end is cut to form again two flexible free ends. One of the ends may be anchored and the other end may be pulled to tension and lock the construct. The at least one flexible coupler may be suture or suture tape or similar material.

The accordion-style weave region may be formed within the body of the fixation device or outside the body of the fixation device. Upon insertion into the bone and tensioning, the accordion-style weave region may reside within the body of the fixation device or outside the body of the fixation device (and within or outside of a bone tunnel).

DETAILED DESCRIPTION

Figure 1:
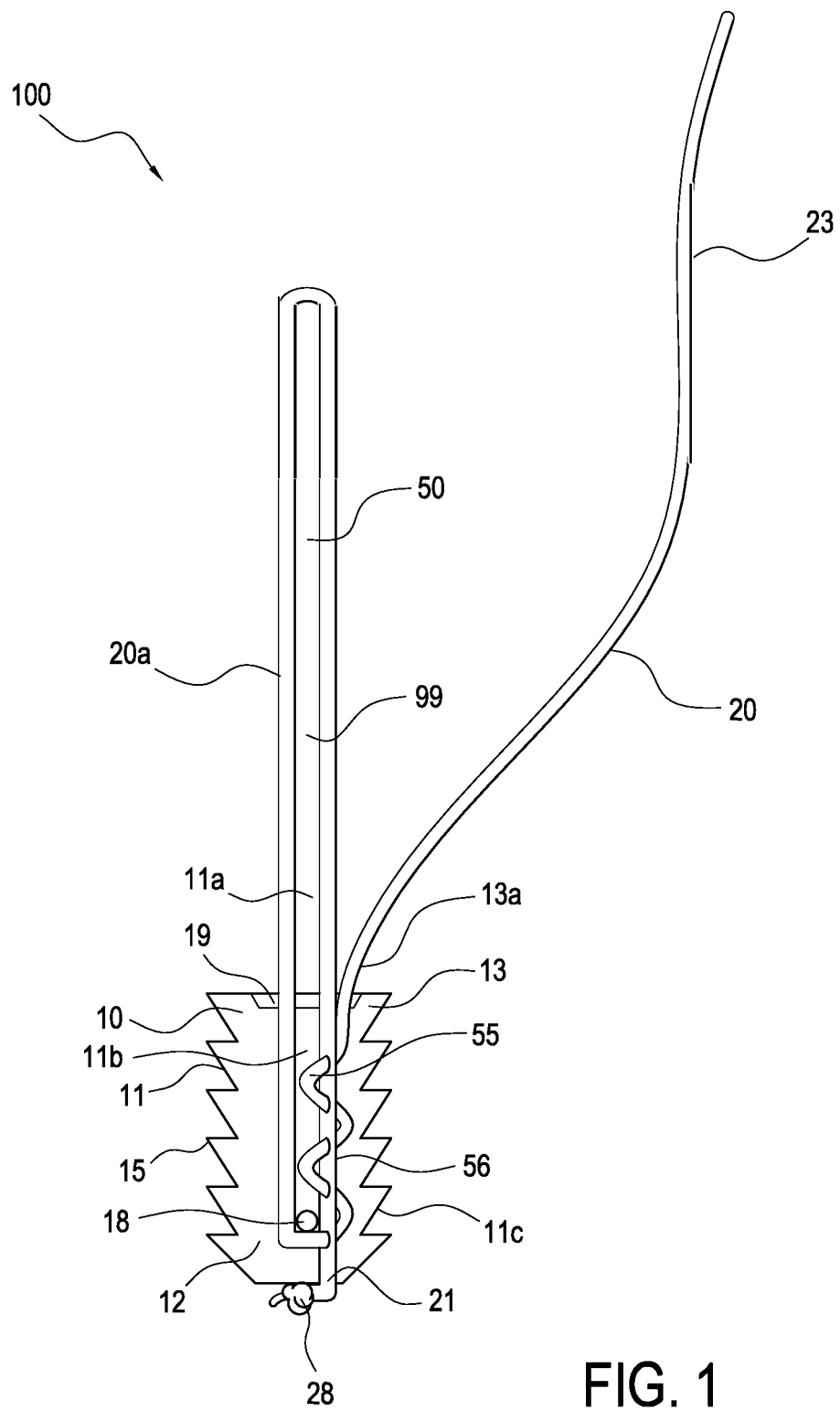
FIG. 1 illustrates a knotless self-locking anchor construct.

The disclosure provides surgical self-locking knotless anchor constructs, surgical systems and assemblies, as well as methods for securing a first tissue to a second tissue, for example, knotless fixation of soft tissue (ligament, tendon, graft, etc.) to bone. The self-locking knotless anchor construct includes a fixation device with a tensionable construct having an adjustable, knotless, flexible, closed loop and a self-locking mechanism.

Fixation devices (tensionable knotless anchors) are inserted into bone with a suture mechanism (tensionable construct) formed of a flexible coupler (a suture tape) provided within the fixation device and a shuttle/pull device (a suture passing instrument) attached to the flexible coupler.

After insertion of the fixation device within bone, the flexible coupler and the shuttle/pull device attached to it allow the formation of an accordion-style weave region within or outside the body of the anchor. The shuttle/pull device is provided attached to the flexible coupler (weaved multiple times through the flexible coupler). The knotless self-locking mechanism of the flexible coupler allows the user (for example, the surgeon) to control the tension of the flexible coupler on the soft tissue to be attached to bone. The flexible coupler may include any flexible material, strand or ribbon such as suture or tape or combinations thereof, for example, multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material.

The flexible coupler may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical self-locking constructs can be used with any type of flexible material or suture known in the art. The shuttle/pull device may be a shuttle/pull suture device such as a FiberLink™ or a Nitinol loop.

Methods of soft tissue repair which do not require tying of knots and allow adjustment of both the tension of the suture and the location of the tissue with respect to the bone, while providing self-locking, are also disclosed. An exemplary method comprises inter alia the steps of: (i) providing a surgical system comprising a fixation device (for example, an anchor) with a flexible coupler (for example, suture tape) and with a shuttle/pull device (a suture passing instrument) attached to the flexible coupler; (ii) inserting the fixation device into bone; (iii) passing the flexible coupler around or through tissue to be fixated (or reattached) to bone, and then through an eyelet/loop of the shuttle/pull device; (iv) subsequently, pulling on the shuttle/pull device to allow the flexible coupler to pass through itself multiple times to form an accordion-style weave region with a plurality of locking points; and (v) pulling on the flexible coupler to lock the construct, to allow the soft tissue to achieve the desired location relative to the bone, and to allow proper tensioning of the final construct.

The flexible coupler may be passed through at least a portion of the body of the fixation device (for example, through a full cannulation of the fixation device, or through a transversal opening at a distal end of the fixation device). Alternatively, the flexible coupler may be fixed to the fixation device (which may be solid or cannulated) by overmolding the coupler to the anchor body or by compressing the coupler against the bone (achieving an interference fit between the fixation device and the bone tunnel, compressing the flexible coupler). The accordion-style weave region may be formed within the body of the fixation device or outside the body of the fixation device. Upon insertion into the bone and tensioning, the accordion-style weave region may reside within the body of the fixation device or outside the body of the fixation device (but within a bone tunnel).

Another exemplary method comprises inter alia the steps of: (i) securing a surgical system to bone, the surgical system comprising a fixation device (for example, an anchor) with a flexible coupler (for example, suture tape) that has two ends and is attached to the flexible coupler, one end of the flexible coupler being passed through the flexible coupler multiple times to form an accordion-style weave region with a plurality of locking points and a first knotless, adjustable, closed, continuous loop with an adjustable perimeter; (ii) bringing together the two ends of the flexible coupler to form a single end; (iii) passing the single end through or around soft tissue; (iv) cutting or removing the connected region to form again the two free ends of the flexible coupler; and (v) pulling on the flexible coupler to lock the construct, to allow the soft tissue to achieve the desired location relative to the bone, and to allow proper tensioning of the final construct.

Referring now to the drawings, where like elements are designated by like reference numerals, FIGS. 1-9 illustrate exemplary knotless self-locking tensionable anchor 100 including exemplary fixation device 10 and flexible coupler 20 (flexible coupling 20) forming tensionable self-locking mechanism 99 (tensionable construct 99) within a body of the fixation device. Knotless tensionable self-locking anchor 100 is illustrated in FIG. 1 after the formation of tensionable self-locking mechanism 99 which includes flexible, closed, knotless, continuous, adjustable loop 50 having an adjustable perimeter and accordion-style weave region 55 (accordion-type weave region 55 or accordion region 55) that creates multiple locking points 56 that lock the construct. One or more flexible couplers 20 may be pre-loaded on the fixation device 10.

Although the embodiments below will be described with reference to a particular embodiment, i.e., with flexible coupler 20 forming tensionable self-locking mechanism 99 (tensionable construct 99) within a body of the fixation device 10, the disclosure has equal applicability to embodiments wherein the tensionable self-locking mechanism 99 (tensionable construct 99) is formed outside a body of the fixation device 10. In addition, a plurality of flexible couplers (for example, two or more flexible couplers) may be pre-loaded onto fixation device 10 and form at least two tensionable self-locking mechanisms 99 (tensionable constructs 99).

Figure 3:
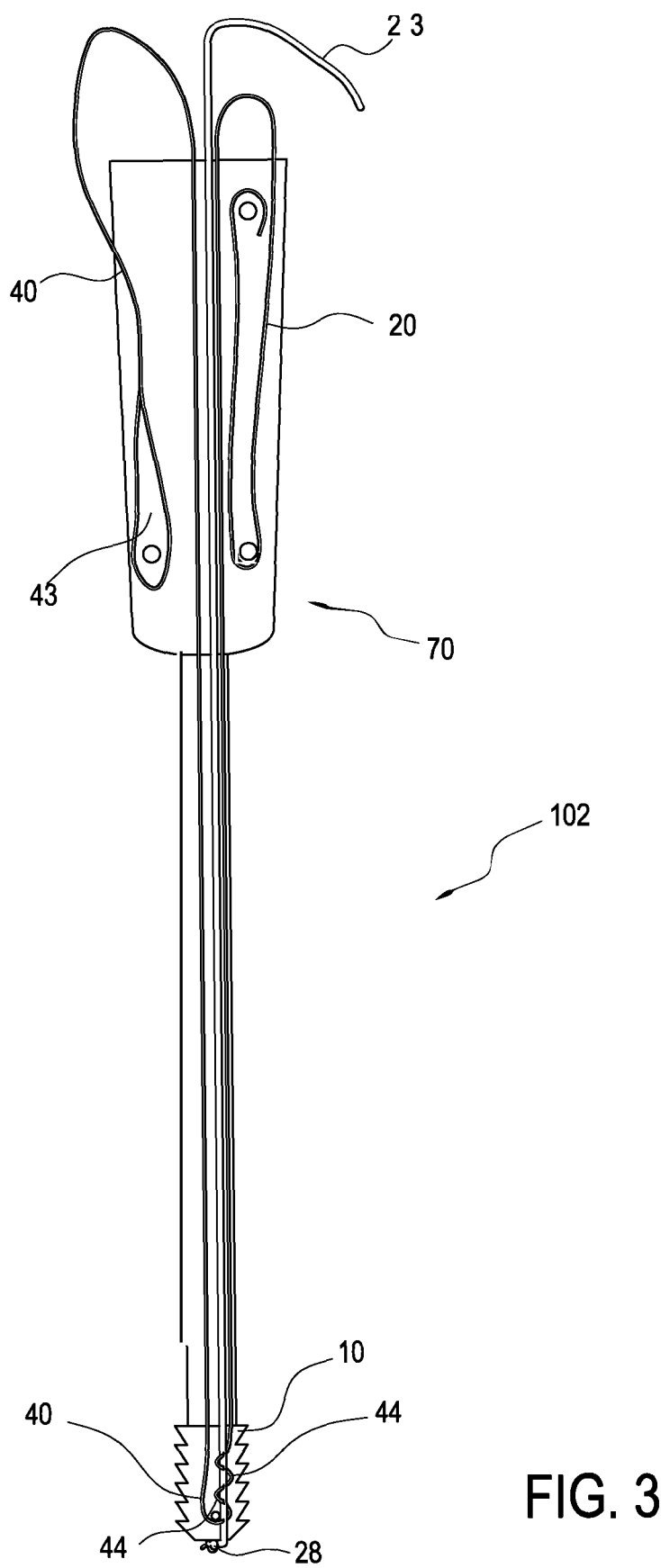
FIG. 3 illustrates a surgical assembly according to an exemplary embodiment.

In the particular exemplary embodiment illustrated in FIG. 1, fixation device 10 is a tensionable knotless anchor having an anchor body 11 provided with a longitudinal axis 11a, a proximal end 13 and a distal end 12, and a plurality of ribs 15 extending circumferentially around it. Openings/channels allow threading flexible couplers and/or suture passing device(s) to pass around post 18, as detailed below. Cannulation 11b extends along the body 11 to allow passage of flexible couplers and of passing devices, as detailed below. A socket 19 may be provided at proximal end 13 and configured to securely engage a tip of a driver, as shown in FIG. 3.

The openings/channels are positioned opposite to each other relative to the post 18 and also symmetrically located relative to the post 18, to allow flexible coupler 20 (suture tape 20) and shuttle/pull device 40 (suture tape passing instrument 40) shown in FIG. 2 to pass and slide therethrough, as also detailed below. The openings/channels extend in a direction about perpendicular to the longitudinal axis 11a, and communicate through recesses with the outer surfaces 11c of anchor body 11. The position and size of the openings/channels and recesses may be determined according to the characteristics of the flexible coupler 20 and shuttle/pull device 40, and of the arthroscopic procedure, and the need to precisely orientate the anchor during insertion to optimize suture tape sliding characteristics.

Anchor 10 may be a screw-in anchor or a push-in style anchor. Anchor 10 may be formed of metal, biocompatible plastic such as PEEK or a bioabsorbable PLLA material or a biocomposite material. Socket 19 at the distal end 13 of the anchor 10 is configured to securely engage a tip of a driver, as detailed below. The socket of the anchor 10 may have any shape adapted to receive a driver tip for pushing tap-in or screw-in style anchors. Tensionable knotless anchor 10 may be made of one or more pieces, or may be provided as an integrated device.

The flexible coupler 20 is provided with two terminal ends, a first end 21 and a second end 23. The first end 21 is a fixed end that forms static knot 28 at the distal end 12, and the second end 23 is a flexible end that is passed multiple times through the flexible coupler 20 to form the flexible, closed, knotless, continuous, adjustable loop 50 having an adjustable perimeter and the accordion-style weave region 55.

The terminal end 23 is woven through the flexible coupler 20, back and through multiple times (for example, five times at five different points) along longitudinal axis 20a of the flexible coupler 20, and in one direction, to form accordion-style weave region 55. Terminal end 23 is passed from a first surface of the flexible coupler 20 to a second, opposite surface of the flexible coupler 20, and for a plurality of times, to form locking points 56 of the accordion-style weave region 55. As detailed below, flexible coupler 20 is passed through itself with the aid of shuttling device 40.

Figure 2:
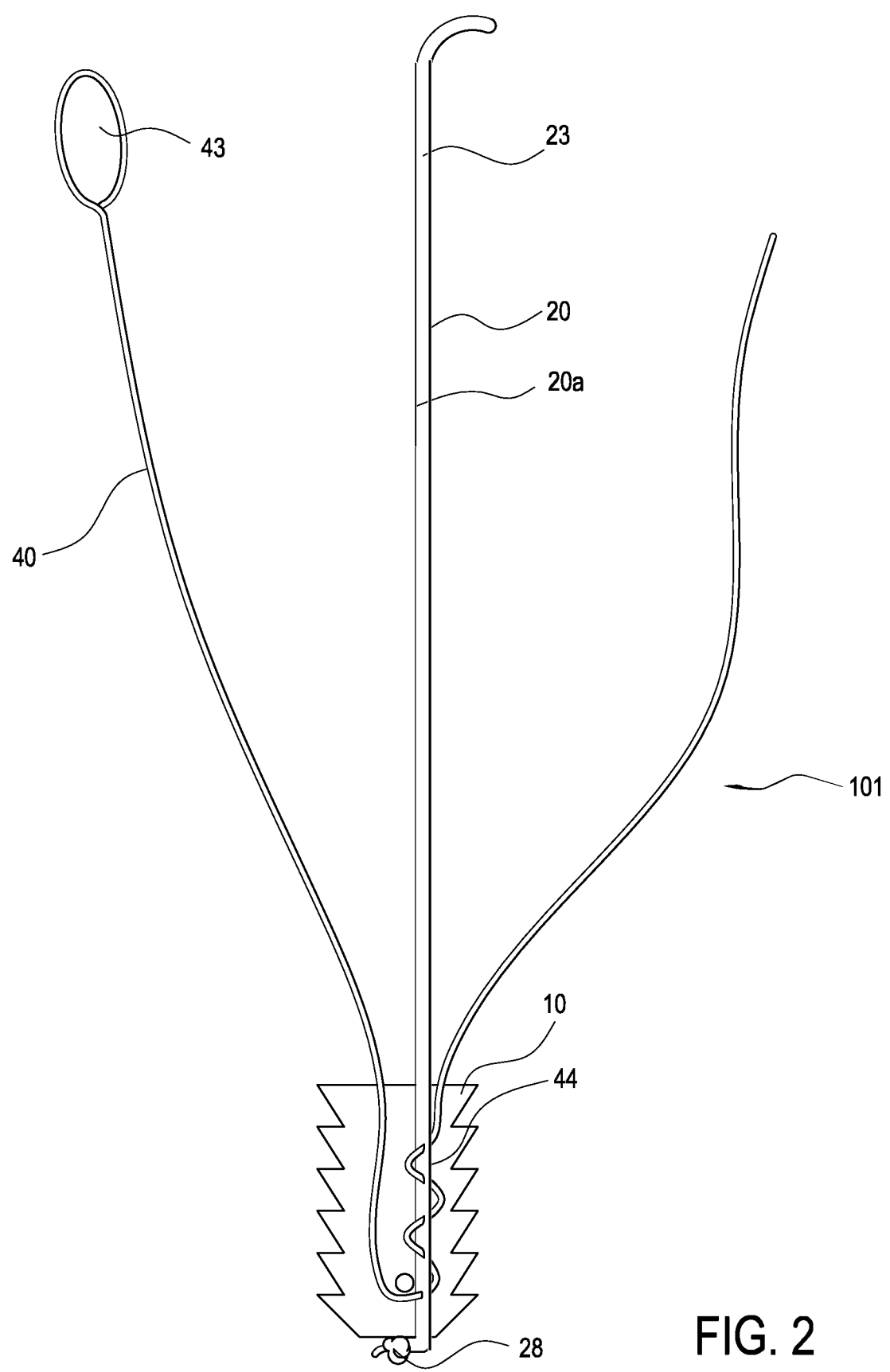
FIG. 2 illustrates a surgical system according to an exemplary embodiment.

Reference is now made to FIG. 2 which illustrates surgical system 101 (surgical assembly 101) with the anchor 10 of FIG. 1 assembled with flexible coupler 20 (suture tape 20) and shuttle/pull device 40 (suture passing instrument or suture passer such as FiberLink™ 40 or a nitinol loop 40) attached to the flexible coupler 20 prior to formation of tensionable self-locking mechanism 99. In particular and exemplary-only embodiments, the flexible coupler 20 is a suture tape 20 and the shuttle/pull device 40 is a suture passing device 40. Surgical system 101 comprises tensionable knotless anchor 10 provided with flexible coupler 20 passing through the body of the tensionable knotless anchor 10 and with shuttle/pull device 40 attached to the flexible coupler 20.

As shown in FIG. 2, shuttle/pull device 40 is provided attached to the flexible coupler 20 by being weaved/passed through the flexible coupler 20 multiple times and at different points to form accordion-style weave region 44 (first accordion-style weave region 44) located within the body of anchor 10. Shuttle/pull device 40 is passed multiple times through the flexible coupler 20, along longitudinal axis 20a of the flexible coupler 20, and in one direction, to form accordion-style weave region 44. Shuttle/pull device 40 is passed from a first surface of the flexible coupler 20 to a second, opposite surface of the flexible coupler 20, and for a plurality of times, to form locking points of the accordion-style weave region 44.

Flexible coupler 20, which is typically braided or multifilament suture tape, is preloaded onto the anchor by tying static knot 28, which prevents flexible coupler 20 from passing through distal blind hole 12a. The flexible coupler 20 may also be preloaded by being molded into the anchor, for example, by insert molding or by any other means known in the art. Flexible coupler 20 passes around post 18, which is large enough to allow flexible coupler 20 to take gradual turns instead of sharp turns. Flexible coupler 20 then passes through cannulation 11b and proximal blind hole 13a. Tensionable knotless anchor 10 is loaded onto a driver (shown in FIG. 3), and flexible coupler 20 is tied to the driver (for example, wrapped around a cleft of the driver) to fasten tensionable knotless anchor 10 securely to the driver. Static end 21 may be secured to the anchor 10 by tying a knot or by any other means known in the art, for example, by insert molding. If a knot is employed, the knot, for example knot 28, may reside within or outside the body 11 of the anchor 10, and may also reside partially within the anchor body 11 and partially outside the anchor body 11, depending on the intended application.

Prior to the fastening of the anchor 10 to the driver, suture passing device 40 (for example, a FiberLink™ or a nitinol loop) is threaded through flexible coupler 20 (i.e., attached to the flexible coupler 20 through accordion-style weave region 44), as shown in FIG. 2. Suture passing device 40 includes an eyelet/loop 43 for passing suture/tape. Suture passing device 40 passes through multiple apertures of flexible coupler 20, traverses around post 18, and through proximal blind hole 13a. Tensionable knotless anchor 10 loaded with flexible coupler 20 attached to the suture passing device 40 is then secured into bone (for example, into a hole/socket/tunnel formed in the bone) by using a driver and surgical assembly 102 (FIG. 3).

Subsequent to the insertion of anchor 10 into a drilled hole in bone, the flexible coupler 20 and suture passing device 40 are released from the driver, and the driver removed. Flexible coupler 20 is then passed through (or around) the tissue 80 which is to be reattached to bone. Flexible coupler 20 is subsequently passed through eyelet/loop 43 of the suture passing device 40. Suture passing device 40 is then pulled, thereby pulling second end 23 of the flexible coupler 20 towards tensionable knotless anchor 10. End 23 is further pulled towards tensionable knotless anchor 10 so that it passes through itself, inside tensionable knotless anchor 10 multiple times, to form accordion-style weave region 55 (second accordion-style weave region 55) which corresponds to first accordion-style region 44 formed by, and with, the passing device 40. The suture passing device 40 has also been further pulled through flexible coupler 20. FIG. 1 illustrates surgical construct 100 with flexible coupler 20 after it has been pulled through itself, creating accordion-style weave region 55 and knotless, closed, adjustable, flexible, continuous loop 50. The suture passing device 40 (not visible anymore in FIG. 1 as it has been completely pulled out of the flexible coupler 20) helps create accordion-style weave region 55 within tensionable knotless anchor 10 by facilitating passing of the flexible coupler 20 through itself.

The anchor may also come without a preloaded shuttle/pull device such as suture passing device 40, i.e., with the accordion-style weave region 55 and the flexible, closed, knotless, continuous, adjustable loop 50 already formed. For example, a pre-assembled variation of the construct/implant may be used for a quick tenodesis application. Fixation device/anchor 10 is inserted into bone, tendon is pulled inside the flexible, closed, knotless, continuous, adjustable loop 50, free end 23 is pulled to shrink the construct and the flexible, closed, knotless, continuous, adjustable loop 50, subsequently compressing the tendon to bone.

FIG. 3 depicts the tensionable knotless anchor 10 with the flexible coupler 20 attached to passing device 40 and inserter driver 70. Flexible coupler 20 is tied to the driver (for example, wrapped around a cleft of the driver) to fasten tensionable knotless anchor 10 securely to driver 70. Prior to securing knotless anchor 10 to the driver, the suture passing device 40 is attached (threaded through flexible coupler 20 to form accordion-style weave region 44) to the flexible coupler 20. The construct is inserted into bone, the flexible coupler 20 untied from the driver, and the driver removed.

After the construct has been inserted into a drilled hole in bone, flexible coupler 20 and passing device 40 are released from the driver, and the driver removed. Flexible coupler 20 is then passed through (or around) the tissue 80 which is to be reattached to bone. Flexible coupler 20 is subsequently passed through eyelet/loop 43 of the suture passing device 40. Suture passing device 40 is then pulled (by a ring, for example), thereby pulling second end 23 of flexible coupler 20 towards tensionable knotless anchor 10.

Once the flexible coupler 20 has been fully passed through itself, the second end 23 (FIG. 1) may be pulled until tissue 80 has been moved to the desired location, such as near a drilled hole in the bone, and the construct locked. Once the desired tension and location is achieved, the second end 23 may be clipped off to complete the soft tissue repair or fixation. In this manner, the flexible coupler 20 is shuttled and pulled (during the surgery) to a desired tension and with the ability to securely lock the final repair/construct.

The constructs, systems, and assemblies of the present disclosure may be employed in numerous knotless soft tissue repairs and fixations, for example, fixation of soft tissue to bone, which may include formation of knotless stitches (simple or mattress stitches), Bankhart and/or SLAP repairs, among many others.

Figure 4:
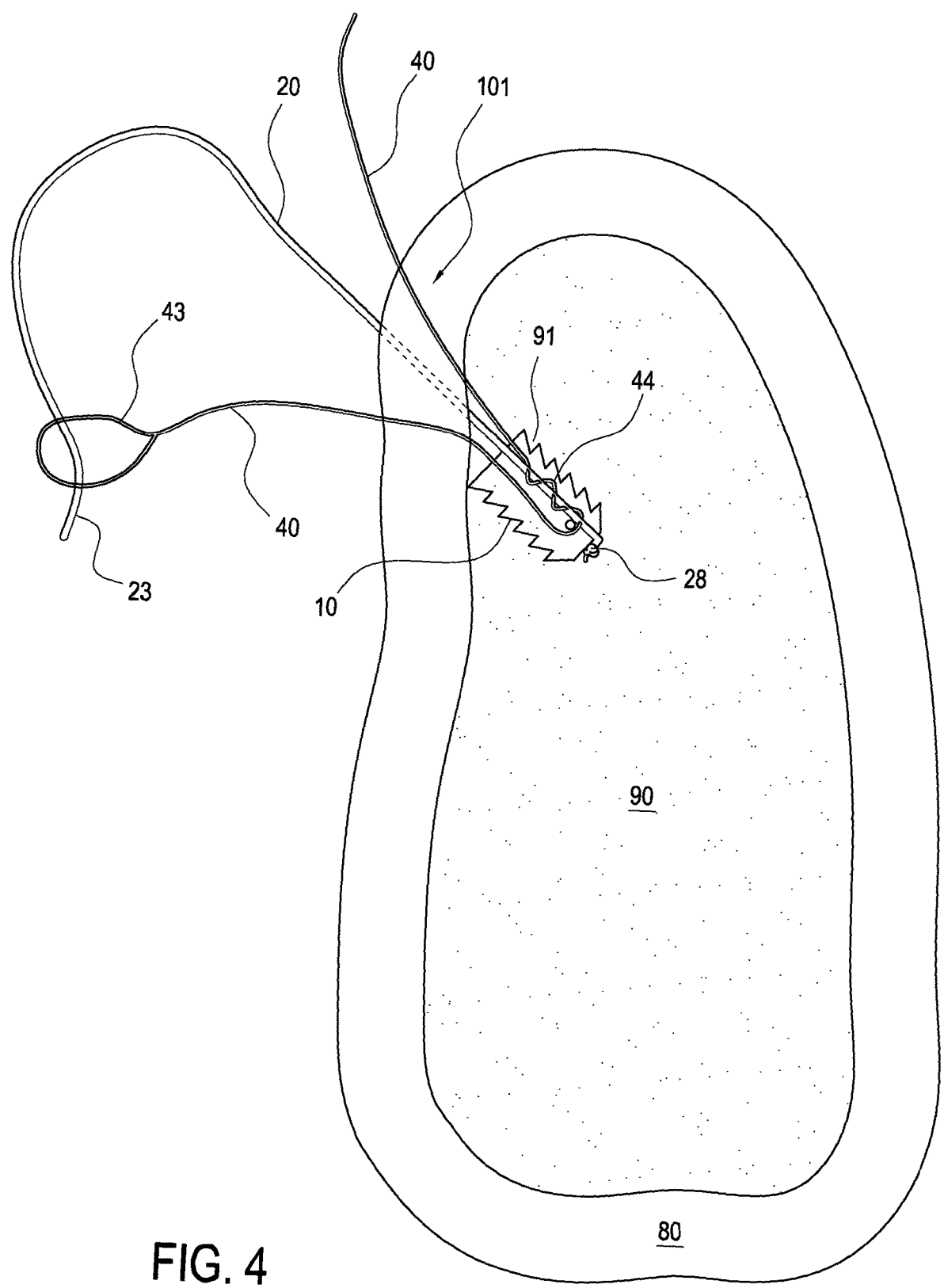
FIGS. 4-6 illustrate subsequent steps of an exemplary method of tissue repair with knotless self-locking anchor constructs.
Figure 5:
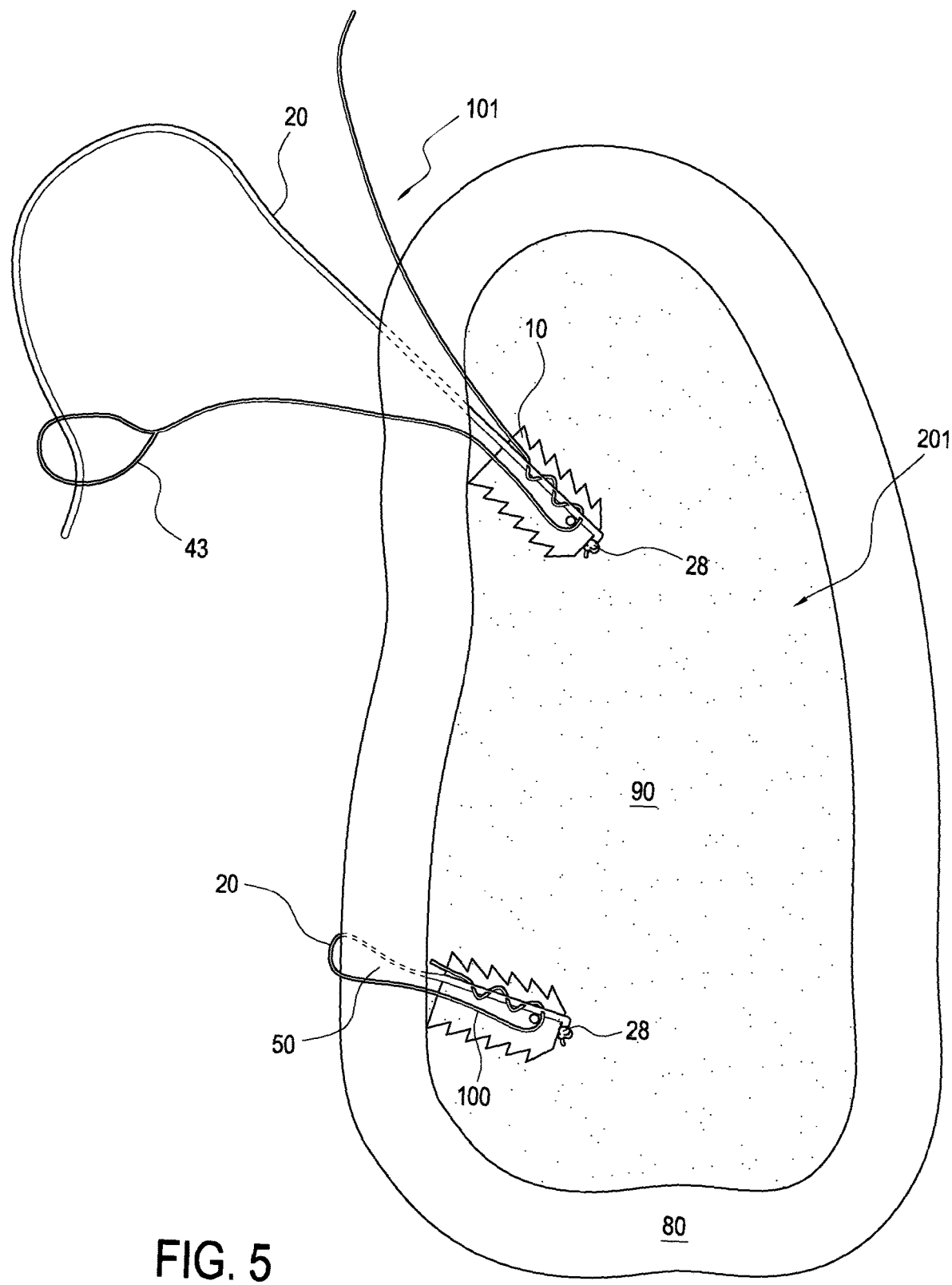

FIGS. 4 and 5 illustrate surgical system 101 of FIG. 2 (with fixation device 10, flexible coupler 20 and shuttling/pulling device 40 attached to the flexible coupler 20) employed in an exemplary method of soft tissue repair (a Bankhart and SLAP repair). A pilot hole may be drilled on the glenoid rim to facilitate anchor insertion and aid in the placement of the anchor onto the face of glenoid 90.

Surgical construct 100 is inserted into the socket in the glenoid by employing driver 70 (shown in FIG. 3). Flexible coupler 20 and shuttling/pulling device 40 are released from the handle of the driver and the driver removed. End 23 of the surgical construct 100 is passed around the tissue 80 (labrum 80) by employing suture passing and retrieving instruments known in the art (for example, a KingFisher® Suture Retriever/Tissue Grasper instrument and a SutureLasso™ instrument). End 23 is then passed through loop 43 of the suture passing device 40. The nitinol wire loop 40 is pulled away from the surgical site, to allow the flexible coupler to accordionize itself within the fixation device 10, or outside the fixation device 10, and form accordion-style weave region 55 within the body of the knotless tensionable anchor 10 of system 100 (as described above with reference to FIGS. 1-3, for example).

Figure 6:
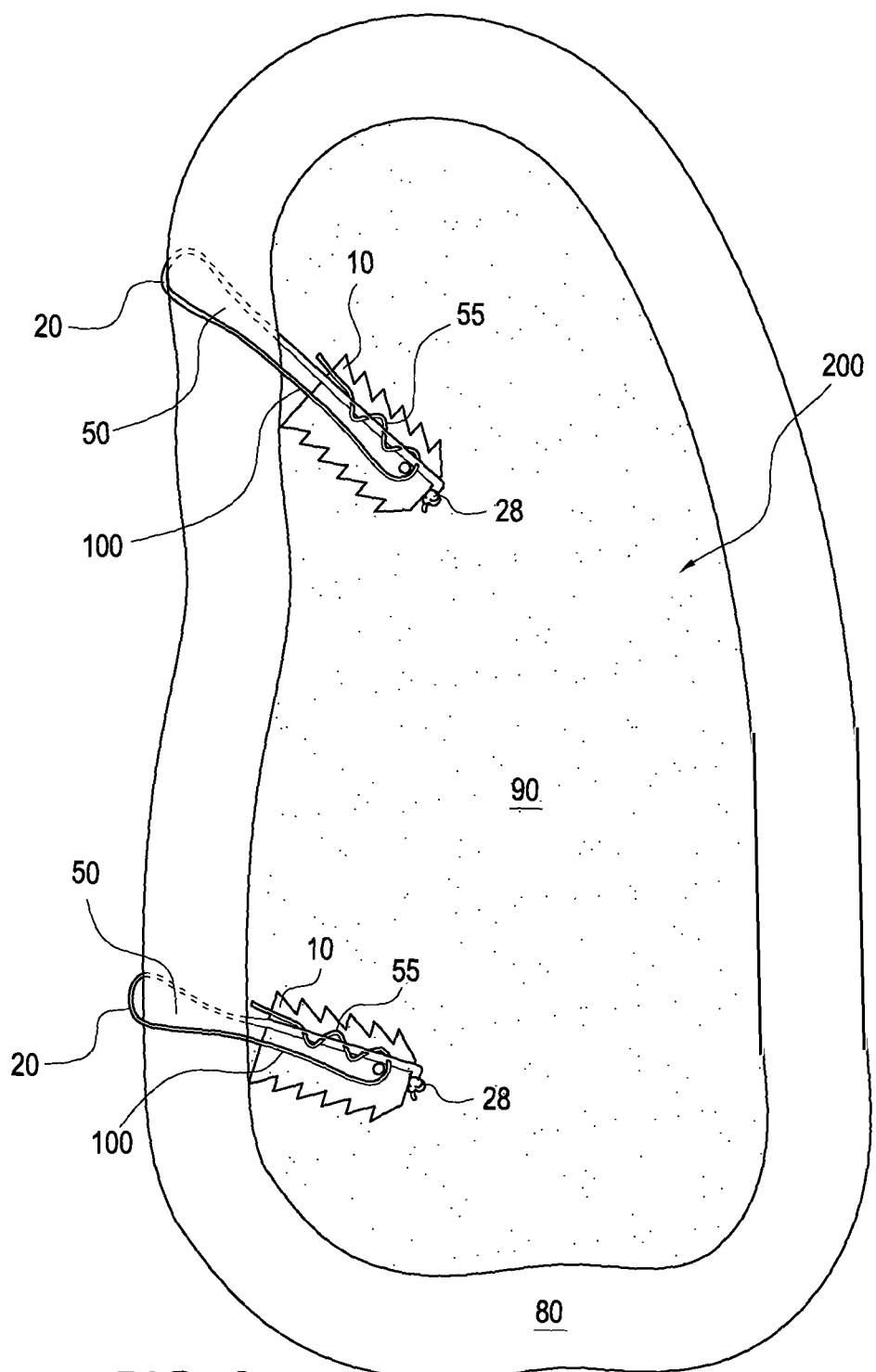
Figure 7:
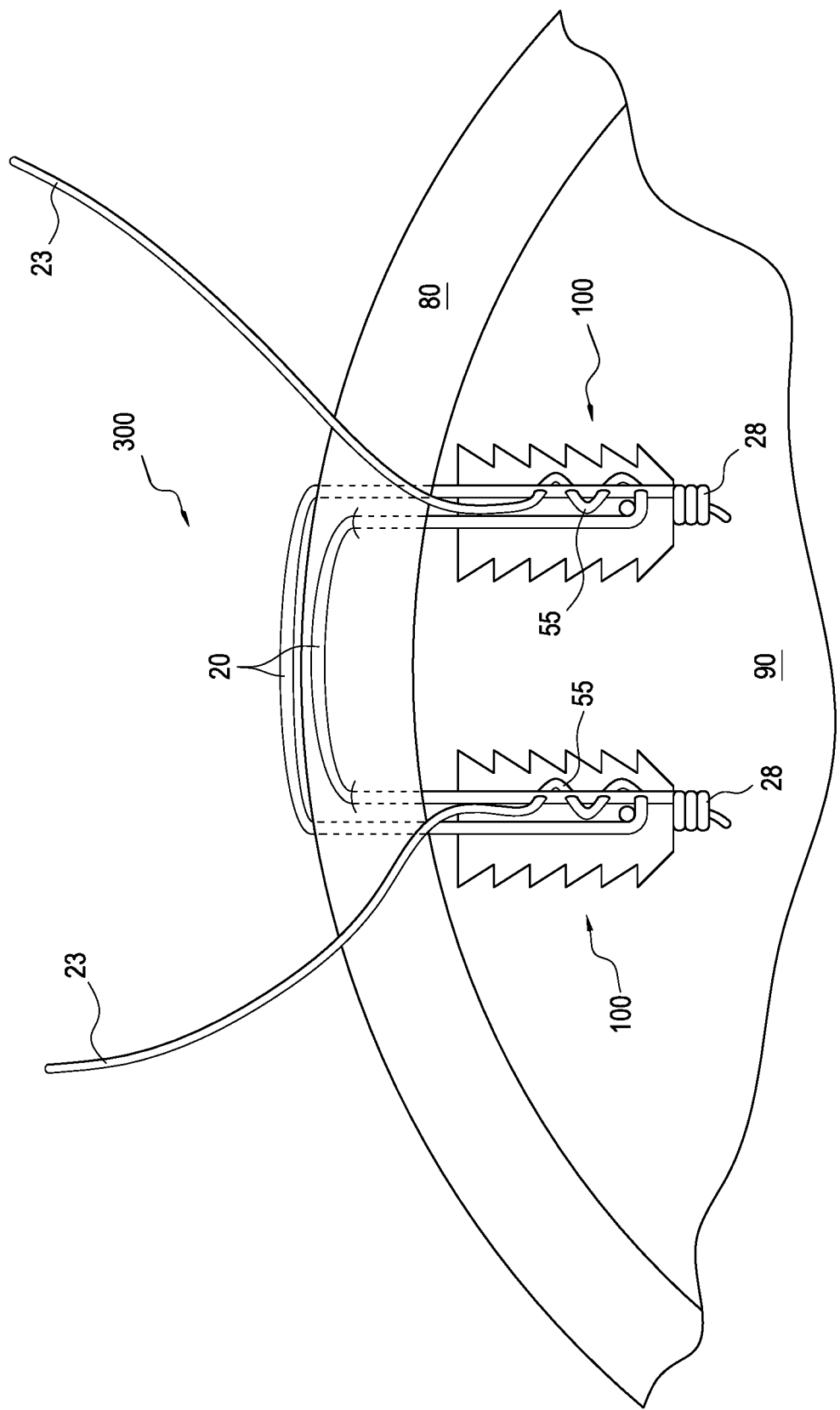
FIG. 7 illustrates another exemplary method of tissue repair with knotless self-locking anchor constructs.

The free end 23 of flexible coupler 20 may then be pulled until the desired tension on the repair is achieved. A knot pusher may be used when applying tension on the repair to divert the force over the anchor and steer the tissue (labrum) 80 to the desired position. The flexible coupler is cut flush with a suture cutter instrument. FIG. 5 illustrate repair 201 with a first knotless tensionable self-locking anchor 100 fully seated onto glenoid 90 and with a second surgical system 101 adjacent the first knotless tensionable self-locking anchor 100 for additional fixation. A plurality of surgical constructs 100 of the present disclosure may be placed according to the specific of each application and as desired. FIG. 6 illustrates repair 200 with two exemplary surgical constructs 100. FIG. 7 illustrates formation of another exemplary repair 300 with constructs 100 of the present disclosure.

Figure 8:
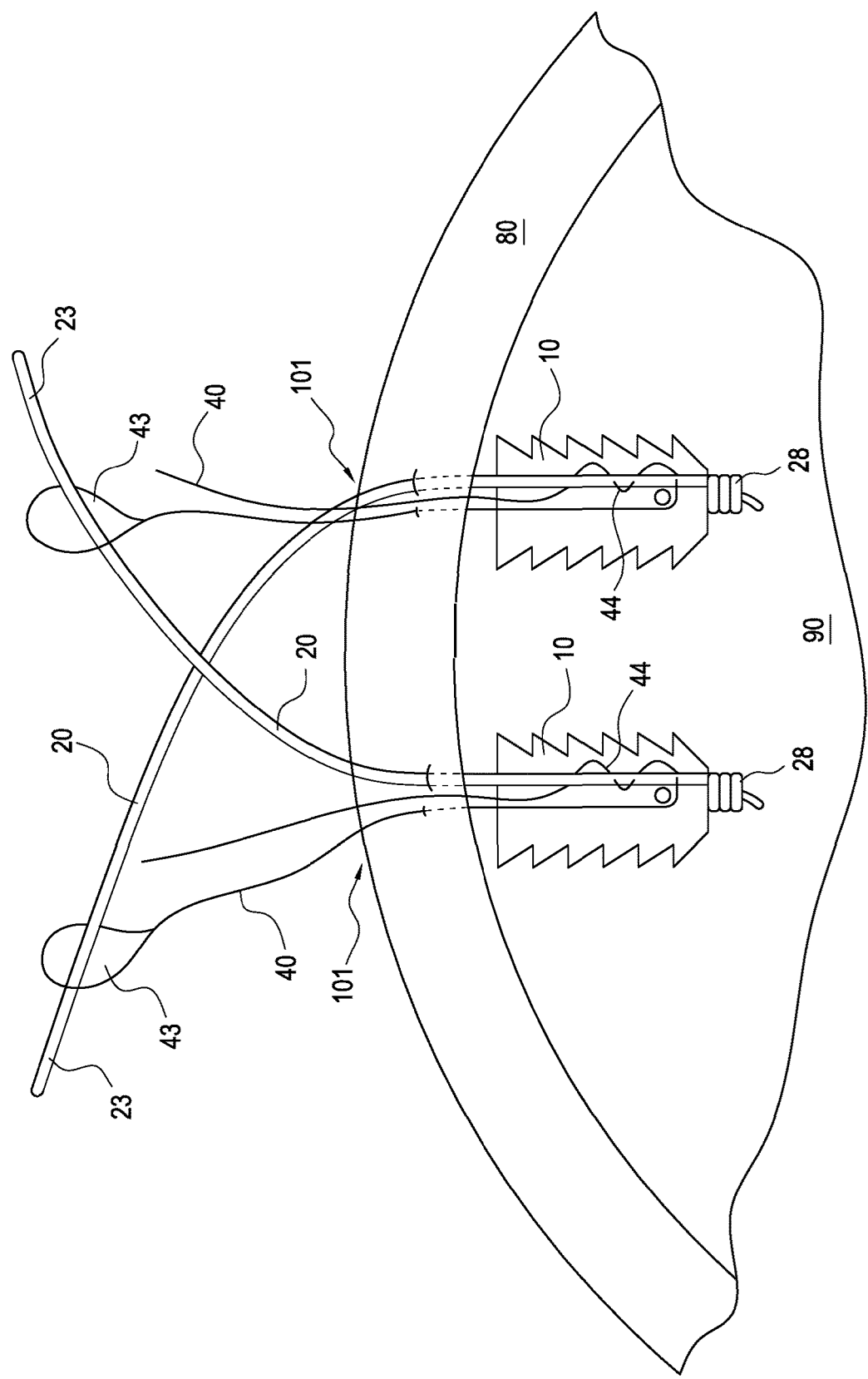
FIGS. 8 and 9 illustrate subsequent steps of an exemplary method of tissue repair with knotless self-locking anchor constructs.
Figure 9:
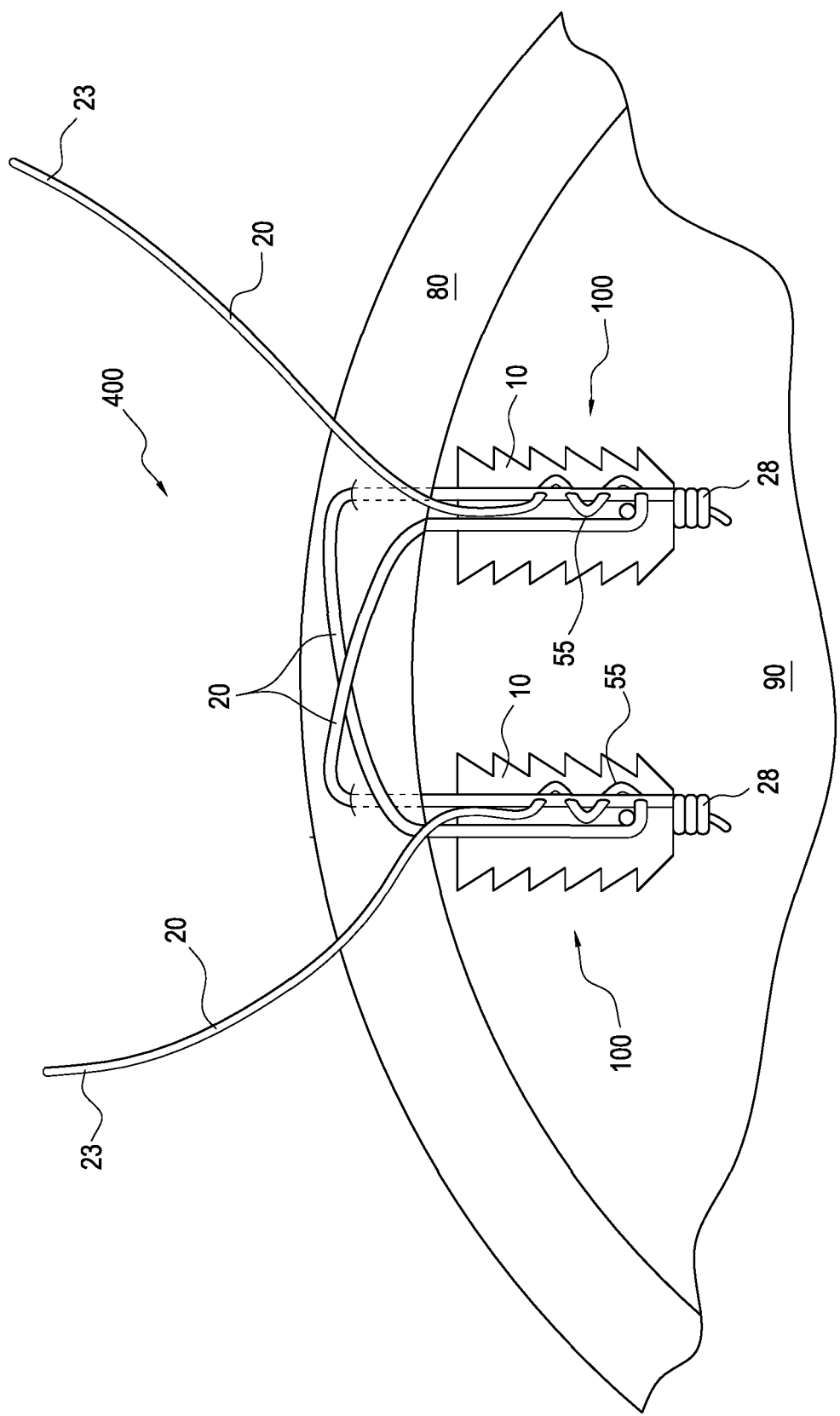

FIGS. 8 and 9 illustrate formation of another exemplary repair 400 with assemblies 101 and constructs 100 of the present disclosure. Two exemplary first and second surgical assemblies 101 are inserted into first tissue 90, each assembly including a knotless anchor 10 preloaded with flexible coupler 20 and shuttle/pull device 40. Each shuttle/pull device forms accordion-type region 44.

An end 23 from one assembly is passed through the loop 43 of the other assembly and vice-versa. Each shuttle/pull device 40 is then pulled out of the site to allow formation of repair 400 with the two flexible couplers of the two constructs 100 being criss-crossed over soft tissue 80, and with two flexible ends 23 for additional pulling/tensioning of the final repair, as shown in FIG. 9.

Figure 10:
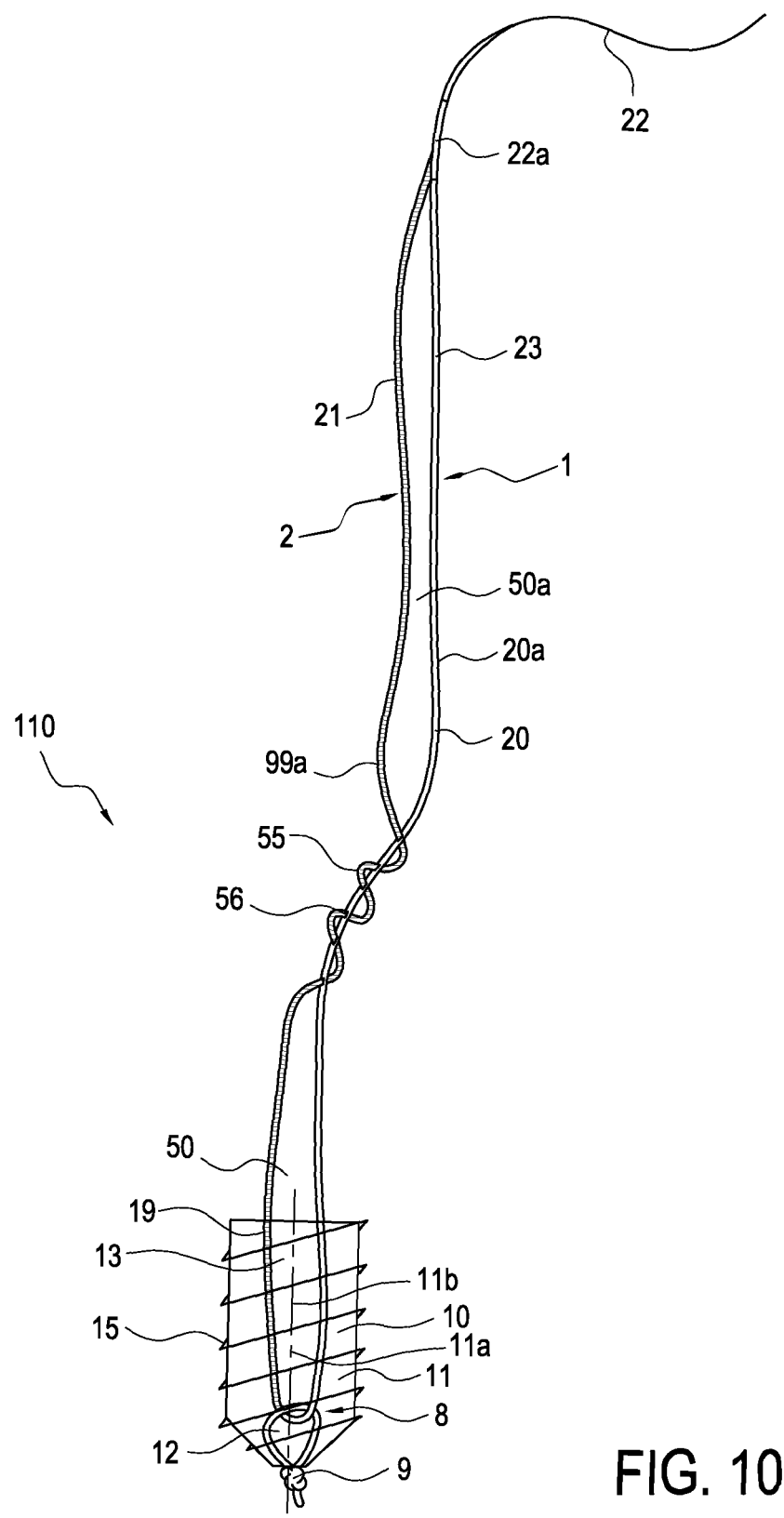
FIG. 10 illustrates a knotless self-locking anchor construct according to an exemplary embodiment.
Figure 11:
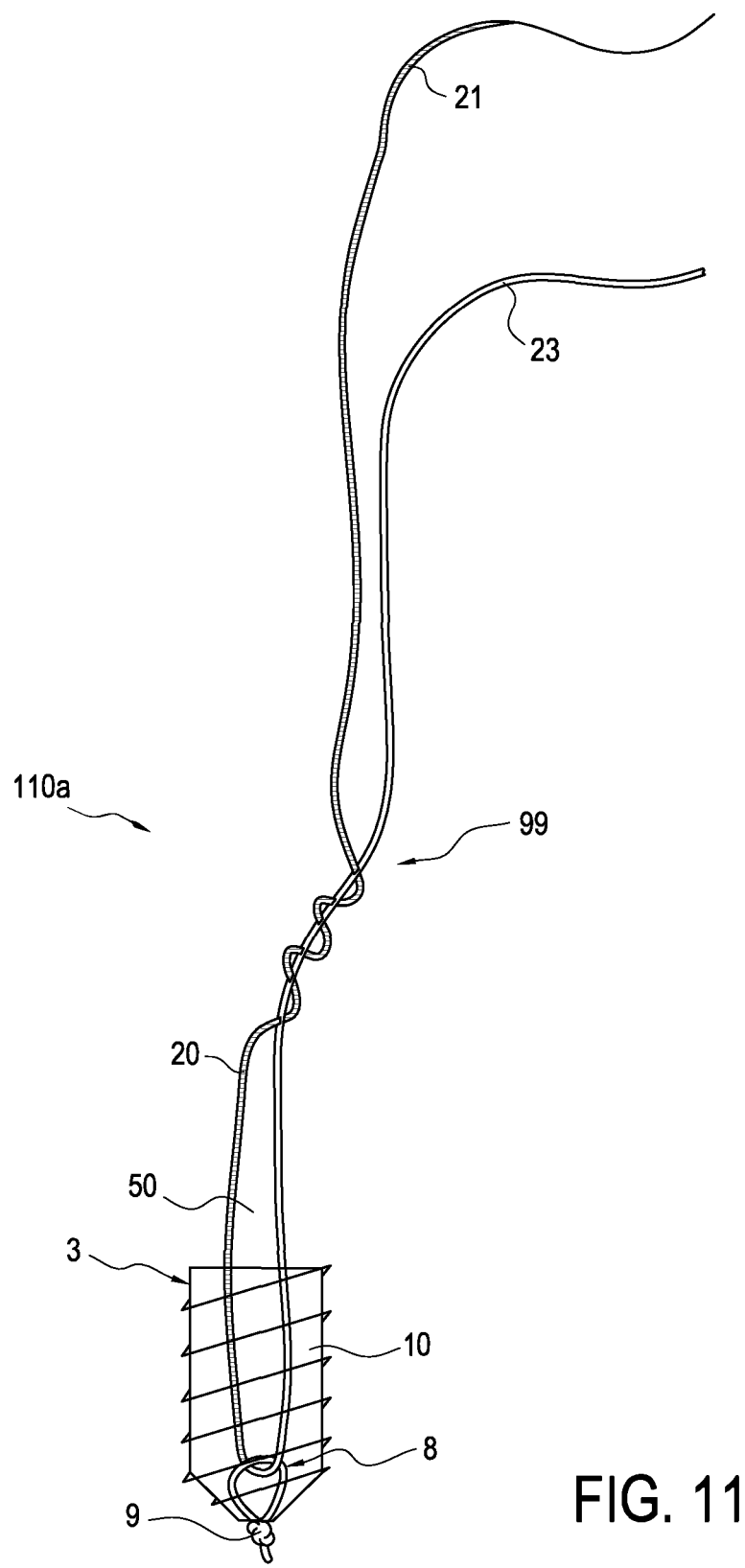
FIG. 11 illustrates the knotless self-locking anchor construct of FIG. 10 without the splice.
Figure 12:
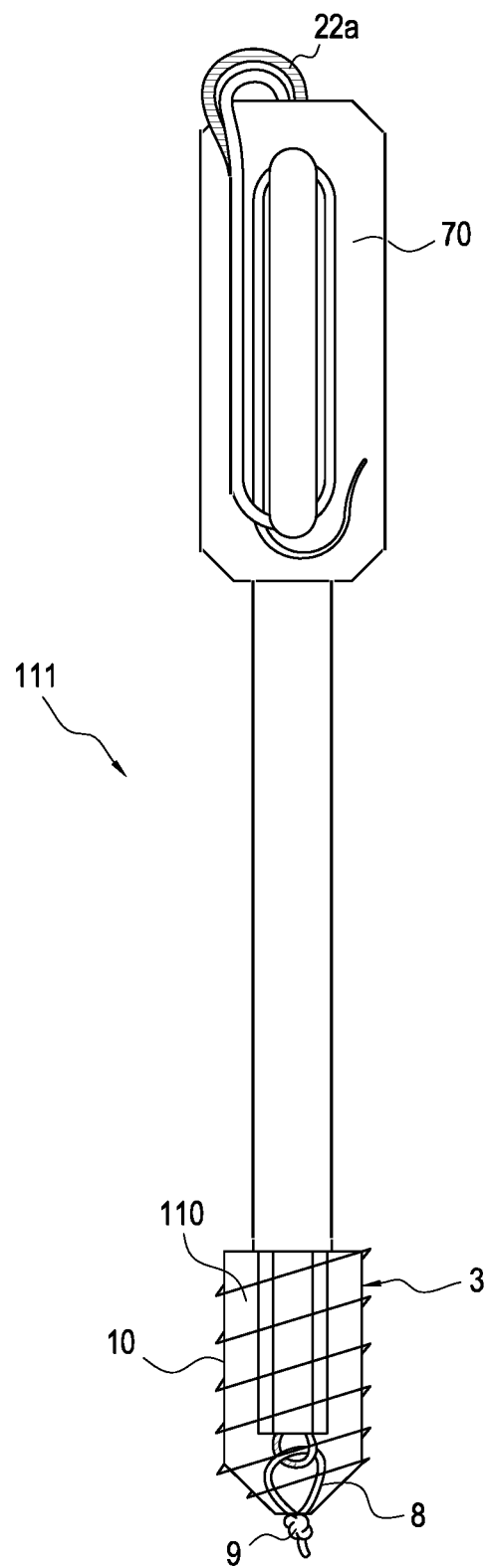
FIG. 12 illustrates a surgical system according to an exemplary embodiment.

FIGS. 10-12 illustrate additional exemplary knotless self-locking tensionable anchor 110 (single-loaded construct 110; knotless self-locking tensionable construct 110; knotless single-loaded self-locking tensionable anchor 110) which is similar in part to construct 100 of FIG. 1 in that it also includes fixation device 10 and flexible coupler 20 as part of a tensionable self-locking mechanism (tensionable construct) attached to the fixation device. Knotless tensionable self-locking anchor 110 differs, however, in that tensionable self-locking mechanism 99a includes two flexible, closed, knotless, continuous, adjustable loops 50, 50a having an adjustable perimeter and accordion-style weave region 55 (accordion-type weave region 55 or accordion region 55) that creates multiple locking points 56 that lock the construct. One or more flexible couplers 20 may be pre-loaded on the fixation device 10.

Flexible coupler 20 (suture tape 20) is also attached to the fixation device 10 in a different manner, i.e., it passes through and slides within the body 11 of the fixation device 10 and is attached to fixation device 10 by being looped through eyelet 8 that forms static knot 9 at distal end 12. Flexible coupler 20 is provided with two terminal ends, a first end 21 and a second end 23 (shown in FIG. 11). The first end 21 and the second end 23 form a single end 22 (shown in FIG. 10) by being brought together (connected or joined) to form single end 22.

Previous to the formation of single end 22, one of the first and second ends 21, 23 is passed through the flexible coupler 20 multiple times to form first flexible, closed, knotless, continuous, adjustable loop 50 having an adjustable perimeter and the accordion-style weave region 55. For example, terminal end 21 is woven through the flexible coupler 20, back and through multiple times (for example, five times at five different points) along longitudinal axis 20a of the flexible coupler 20, and in one direction, to form accordion-style weave region 55 and first flexible, closed, knotless, continuous, adjustable loop 50. Terminal end 21 is passed from a first surface of the flexible coupler 20 to a second, opposite surface of the flexible coupler 20, and for a plurality of times, to form locking points 56 of the accordion-style weave region 55.

Subsequent to the formation of first flexible, closed, knotless, continuous, adjustable loop 50 having an adjustable perimeter and the accordion-style weave region 55, the two ends 21, 23 are brought together to form a single end 22. The two ends may be brought together or connected by fusion, melting, knotting, splicing, joining, suturing, or any known method in the art, to form a connected region 22a. The connected region 22a may be a splice 22a located between ends 21, 23 and single end 22. Single end 22 (spliced end 22) facilitates passing of the end through soft tissue to be fixated, and as detailed below. The first end 21 and the second end 23 form single end 22 and define second flexible, closed, knotless, continuous, adjustable loop 50*a* having an adjustable perimeter (located in between the accordion-style weave region 55 and the splice 22*a*, as shown in FIG. 10).

The two terminal ends 21, 23 may be brought together/coupled/joined by gluing, bonding, splicing, knotting, fusing, melting, heating, or by any other known method in the art, to form single end 22. In certain embodiments, the connecting of the ends may be accomplished by splicing (such as, for example, to form splice 22*a*). The ends may be first joined together to form a single end and then the single end may be connected/attached to a suture passing device, such as needle, for example.

FIG. 11 illustrates self-locking tensionable anchor 110*a* which is about similar to self-locking tensionable anchor 110 but differs from it in that tensionable self-locking mechanism 99 (tensionable construct 99) includes only flexible, closed, knotless, continuous, adjustable loop 50 having an adjustable perimeter and accordion-style weave region 55 (accordion-type weave region 55 or accordion region 55) that creates multiple locking points 56 that lock the construct. Flexible, closed, knotless, continuous, adjustable loop 50*a* has been removed by the removal of splice 22*a* and single end 22, to form again the two free ends 21, 23 of the flexible coupler 20.

Reference is now made to FIG. 12 which illustrates surgical system 111 with exemplary knotless self-locking tensionable anchor construct 110 of FIG. 10 with the flexible coupler 20 attached to inserter driver 70. Flexible coupler 20 is provided with connected region 22*a* (for example, splice 22*a*) and single end 22 which is tied to the driver (for example, wrapped around a cleft of the driver) to fasten tensionable knotless anchor 110 securely to driver 70. Prior to securing knotless anchor construct 110 to the driver, the flexible coupler 20 forms accordion-style weave region 55 and first and second flexible, closed, knotless, continuous, adjustable loops 50, 50*a*. The construct is inserted into bone, the flexible coupler 20 untied from the driver, and the driver removed.

After the construct has been inserted into a drilled hole in bone, flexible coupler 20 is released from the driver, and the single spliced end 22 is then passed through (or around) the tissue 80 which is to be reattached to bone. Once the flexible single end 22 has been passed through or around tissue, the splice 22*a* is removed (for example, cut) to allow formation of two flexible separate ends 21, 23. One of the ends 21, 23 may be anchored and the other of the ends 21, 23 may be pulled until tissue 80 has been moved to the desired location, such as near a drilled hole in the bone, and the construct locked. Once the desired tension and location is achieved, the pulling end may be clipped off to complete the soft tissue repair or fixation. In this manner, the flexible coupler 20 is shuttled and pulled (during the surgery) to a desired tension and with the ability to securely lock the final repair/construct.

Figure 13:
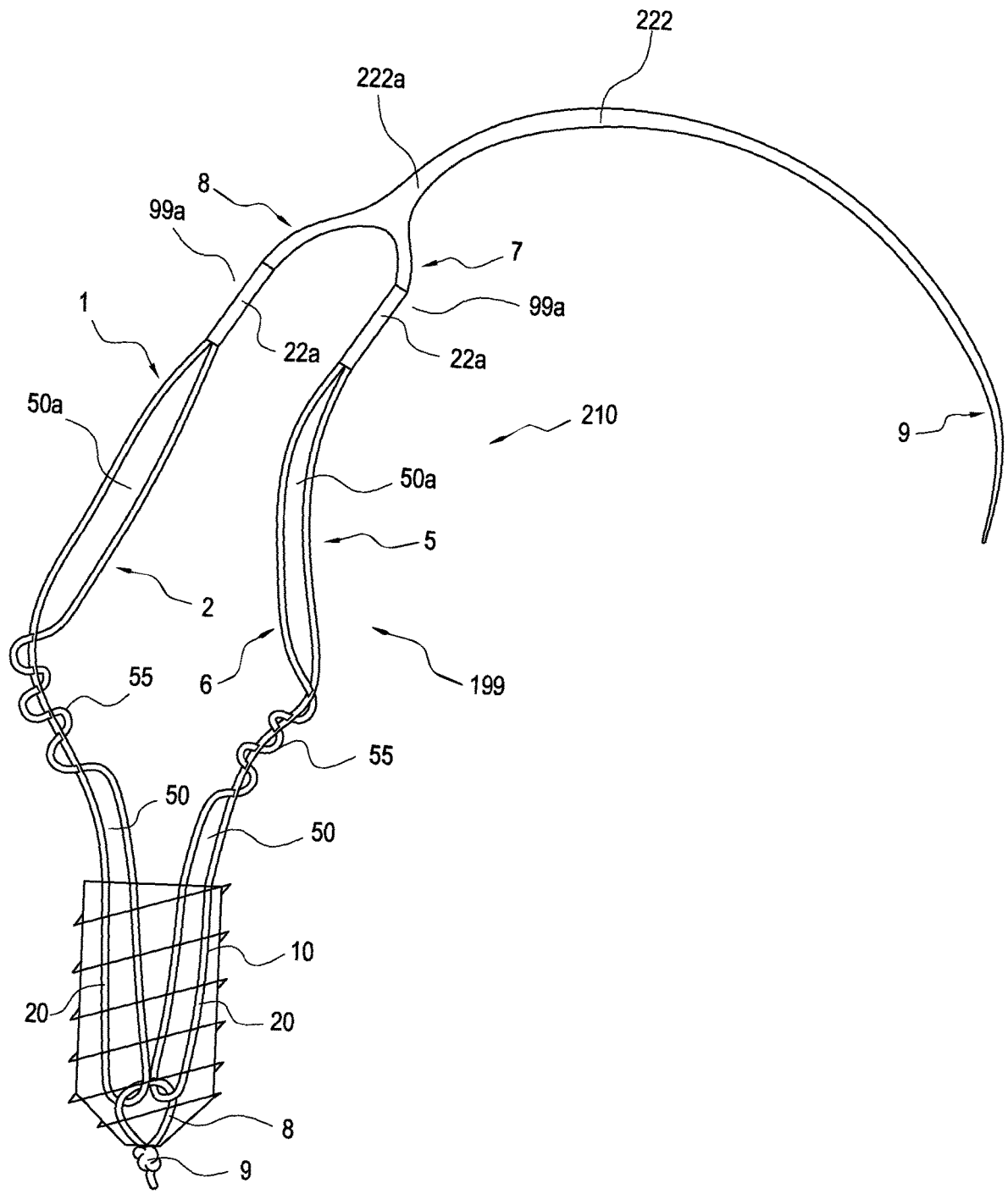
FIG. 13 illustrates a knotless self-locking anchor construct according to another exemplary embodiment.

FIG. 13 illustrates another exemplary knotless self-locking tensionable anchor 210 (multiple-loaded construct 210; knotless self-locking tensionable construct 210; knotless multiple-loaded self-locking tensionable anchor 210) which is about similar to construct 110 of FIG. 10 in that it also includes an exemplary fixation device 10 and a single spliced end 22. However, exemplary knotless self-locking tensionable anchor 210 includes two or more flexible couplers 20 forming tensionable self-locking mechanisms 199 formed of two or more tensionable self-locking mechanisms 99*a* (tensionable construct 99*a*) attached to the fixation device. For example, exemplary knotless self-locking tensionable anchor 210 is a double-loaded construct with two flexible couplers 20 each forming a tensionable self-locking mechanism 99*a* (tensionable construct 99*a*).

The two terminal ends 21, 23 of each of the two flexible couplers may be brought together/coupled/joined by gluing, bonding, splicing, knotting, fusing, melting, heating, or by any other known method in the art, to form single end 222. In certain embodiments, the connecting of the ends may be accomplished by splicing (such as, for example, to each form splice 22*a*). The ends may be first joined together to form a single end and then the single end may be connected/attached to a suture passing device, such as needle, for example. Alternatively, all four ends may be brought together/coupled/joined at the same time.

Figure 14:
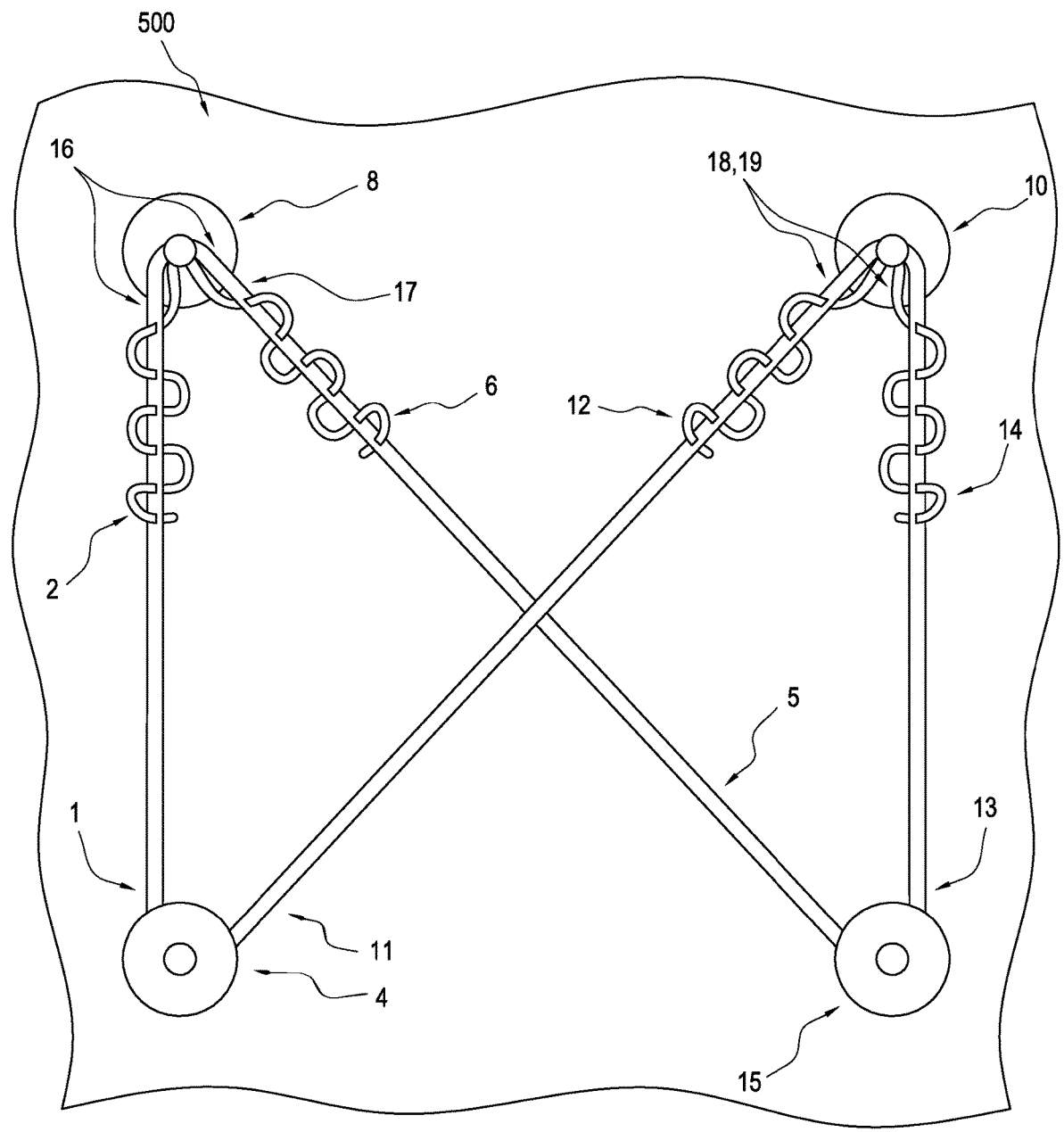
FIGS. 14-19 illustrate steps of exemplary methods of tissue repair with knotless self-locking anchor constructs.

Knotless tensionable self-locking anchor 210 is illustrated in FIG. 14 after the formation of tensionable self-locking mechanisms 99*a* which each includes two flexible, closed, knotless, continuous, adjustable loops 50, 50*a* having an adjustable perimeter and accordion-style weave region 55 (accordion-type weave region 55 or accordion region 55) that creates multiple locking points 56 that lock the construct. Each of the flexible couplers 20 may be pre-loaded on the fixation device 10 by attachment to eyelet 8.

Each of the two flexible couplers 20 defines first and second flexible, closed, knotless, continuous, adjustable loops 50, 50*a* having an adjustable perimeter and accordion-style weave region 55, and a connected region 22*a* (a splice 22*a*) terminating in a single spliced end 22. The two single spliced ends 22 from each construct are then brought together (spliced, for example) to form a connected region 222*a* (splice 222*a*) and a single spliced end 222 of construct 210. As in the previously-described embodiment, once the single spliced end 222 has been passed through or around tissue to be secured, at least one of the splices 22*a*, 222*a* may be removed, allowing the construct to form again at least two flexible separate ends, for example 2, 3, or 4 separate flexible ends to continue the repair.

The constructs, systems, and assemblies of the present disclosure may be employed in various knotless soft tissue repairs and fixations, for example, fixation of soft tissue to bone, which may include formation of knotless stitches (simple or mattress stitches), Bankhart and/or SLAP repairs, among many others.

Figure 15:
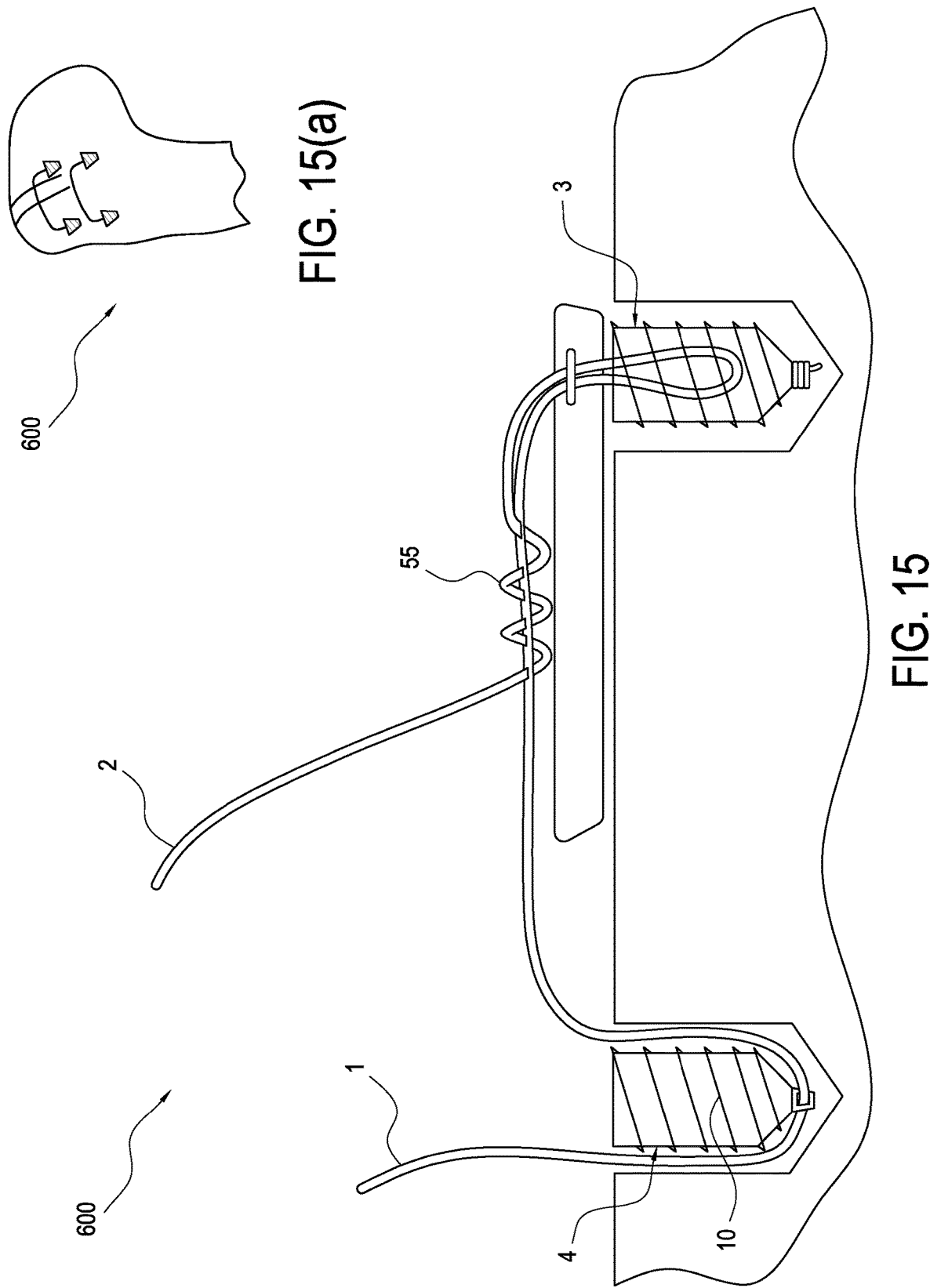
Figure 16:
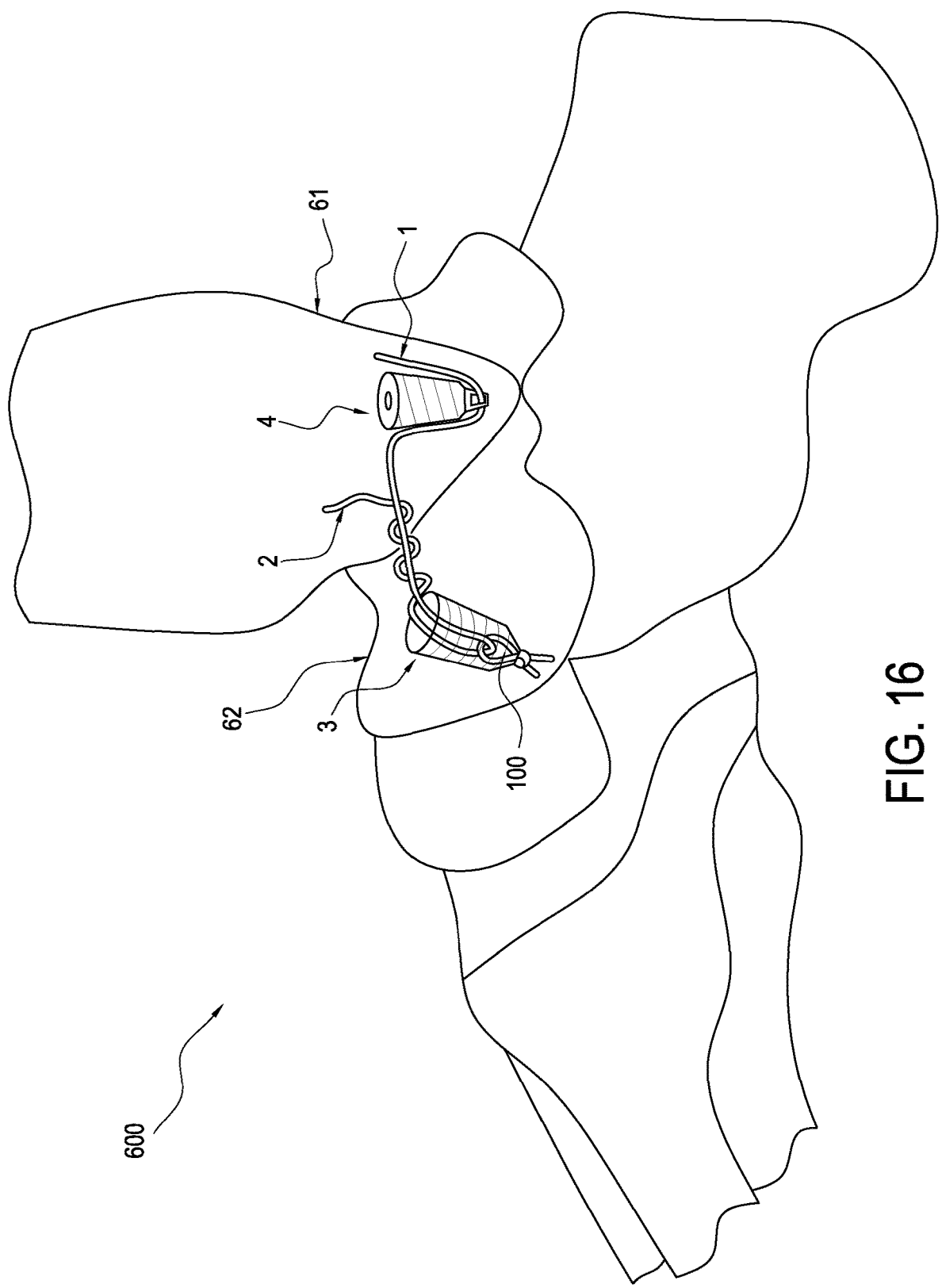

FIGS. 14-16 illustrate exemplary tissue repairs with surgical constructs of the present disclosure. In an exemplary tension bridge repair 500 (FIG. 14), a device is used to reattach tendon, ligament, or soft tissue to bone, bone to bone, or soft tissue to soft tissue. The device is comprised of an anchor body, and a flat tape like flexible coupler, and/or round flexible coupler. The flexible coupler is passed down through the cannulation of the anchor body, looped through an eyelet inside the anchor body, and back out the cannulation of the anchor body. The eyelet inside the anchor body is comprised of a similar flat, tape, and/or round flexible coupler that is attached to the anchor body. End one (1) of the flexible coupler is passed down through the eyelet within the anchor body, and back up exiting the anchor through the cannulation in which it entered. The opposite end of the flexible coupler (End 2), is woven through the flexible coupler in an accordion/pleat weave fashion to create a self-locking mechanism between ends one (1) and two (2). Ends one (1) and two (2) are then spliced together to facilitate passing through tissue. Once passing through desired soft tissue is complete, the splice is cut, making two (2) free ends. End one (1) is then anchored. Tension is then applied to end two (2), shrinking the collapsible loop. Alternatively, no splice or and/or passing through soft tissue is necessary. The device can be used to attach bone to bone. The anchor (3) can be placed in bone, end one (1) can be placed in another anchoring device (4) and attached to bone. Tension can then be applied to end two (2), shrinking the collapsible loop.

An exemplary tension bridge technique for rotator cuff repair 600 (FIGS. 15 and 15*a*) includes the following steps:
1. Prepare the footprint for the rotator cuff in standard fashion.
2. Prepare an anteromedial bone socket with a punch along the articular margin. Insert the first Tension Bridge through a percutaneous stab incision.
3. Retrieve the suture(s) through the lateral cannula.
4. Pass the single tail of the 4 spliced sutures through the rotator cuff.
5. Retrieve the tail through the anterior cannula.
6. Repeat these steps 1-3 for the posteromedial anchor.
7. Retrieve the suture tail from posteromedial anchor through the percutaneous stab incision.
8. Cut the suture splices from both anchors, creating eight (8) sutures.
9. Pull one solid blue, and one solid white suture from each anchor out of the lateral cannula.
10. Load these sutures into a swivel lock (or similar) anchor.
11. Create a socket for the posterolateral anchor using a punch, insert the anchor, then cut the 2 suture tails from this anchor.
12. repeat steps 8-10 for anterolateral anchor.
13. You will now have 4 striped tails remaining. Pull these remaining sutures out of the lateral cannula and pull tension on these sutures to achieve desired tension of repair.
14. Cut striped sutures to complete procedure.

An exemplary double Tension Bridge repair (shown in FIGS. 14-16) is conducted by employing one or more devices/constructs of the present disclosure to reattach tendon, ligament, or soft tissue to bone, bone to bone, or soft tissue to soft tissue. The device is comprised of an anchor body, and a flat tape like flexible coupler, and/or round flexible coupler. The flexible coupler is passed down through the cannulation of the anchor body, looped through an eyelet inside the anchor body, and back out the cannulation of the anchor body. The eyelet inside the anchor body is comprised of a similar flat, tape, and/or round flexible coupler that is attached to the anchor body. End (1) of the flexible coupler is passed down through the eyelet within the anchor body, and back up exiting the anchor through the cannulation in which it entered. The opposite end of the flexible coupler (End 2), is woven through the flexible coupler in an accordion/pleat weave fashion to create a self-locking mechanism between ends one (1) and two (2). This process is repeated with a second flexible couple within the same anchor end (5) and end (6). End (1), end (2), end (5), and end (6), are then spliced together to form one suture end (9), to facilitate passing through tissue. Once the suture end (9) is passed, the suture is cut at splices to form four free ends (1), (2), (5), (6). The portion cut off the anchor, end (7), end (8), end (9) are discarded. The entire process is then repeated with a second anchor (10) placed parallel to the first anchor (3), suture tail passed through tissue, splice cut. This leaving eight total sutures through tissue, (1), (2), (5), (6), (11), (12), (13), (14), on 2 separate planes. End (1) and end (11) are then anchored (4). End (13), and end (5), are then anchored (15). Ends (2), (6), (12), (14) can then be pulled to shrink the four collapsible loops, (16), (17), (18), (19), and achieve final tension of construct to complete repair.

FIG. 15(*a*) shows an example of the device of the present disclosure secured into humerus for rotator cuff repair. In FIG. 15, tension is applied to end 2 to collapse the loop and tighten the construct. The flexible coupler is threaded through an eyelet of anchor 4 and locked into bone.

The self-locking tensionable construct 99, 99*a*, 199 of the present disclosure may be employed in a method of bunion repair as described in U.S. Pat. No. 7,875,058 issued Jan. 25, 2011, and/or in a method of Lisfranc repair as described in U.S. Pat. No. 7,901,431 issued Mar. 8, 2011, the disclosures of both of which are incorporated by reference in their entirety herewith (wherein the flexible coupler of self-locking tensionable construct 99, 99*a*, 199 would be attached to first and second buttons). Similarly, the self-locking tensionable construct 99, 199 of the present disclosure may be employed in a method of fixation of bone to bone as described in U.S. Pat. No. 9,005,245 issued Apr. 14, 2015, the disclosure of which is incorporated by reference in its entirety herewith (wherein the flexible coupler of self-locking tensionable construct 99, 99*a*, 199 would be attached to first and second buttons, so that the flexible coupler extends between a plurality of bone tunnels and secures at least a first bone to a second bone in a self-locking manner).

FIG. 16 illustrate an exemplary method of ankle syndesmosis self-locking repair 600 with constructs of the present disclosure formed of self-locking tensionable construct 99, 99*a*, 199 with a flexible coupler 20 attached to different fixation devices. Constructs are secured within the fibula 61 and talus 62 of an ankle joint.

Figure 17:
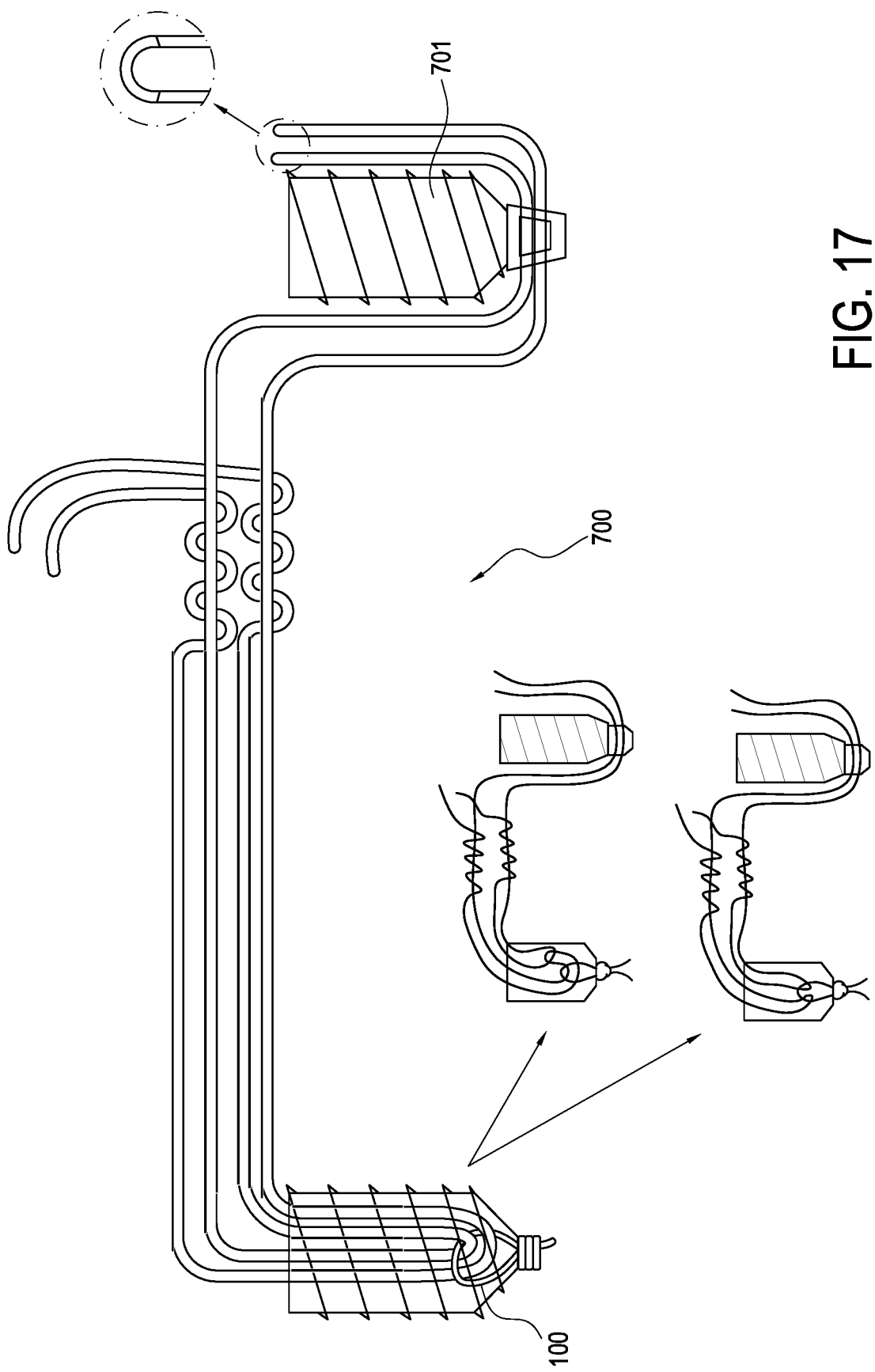
Figure 18:
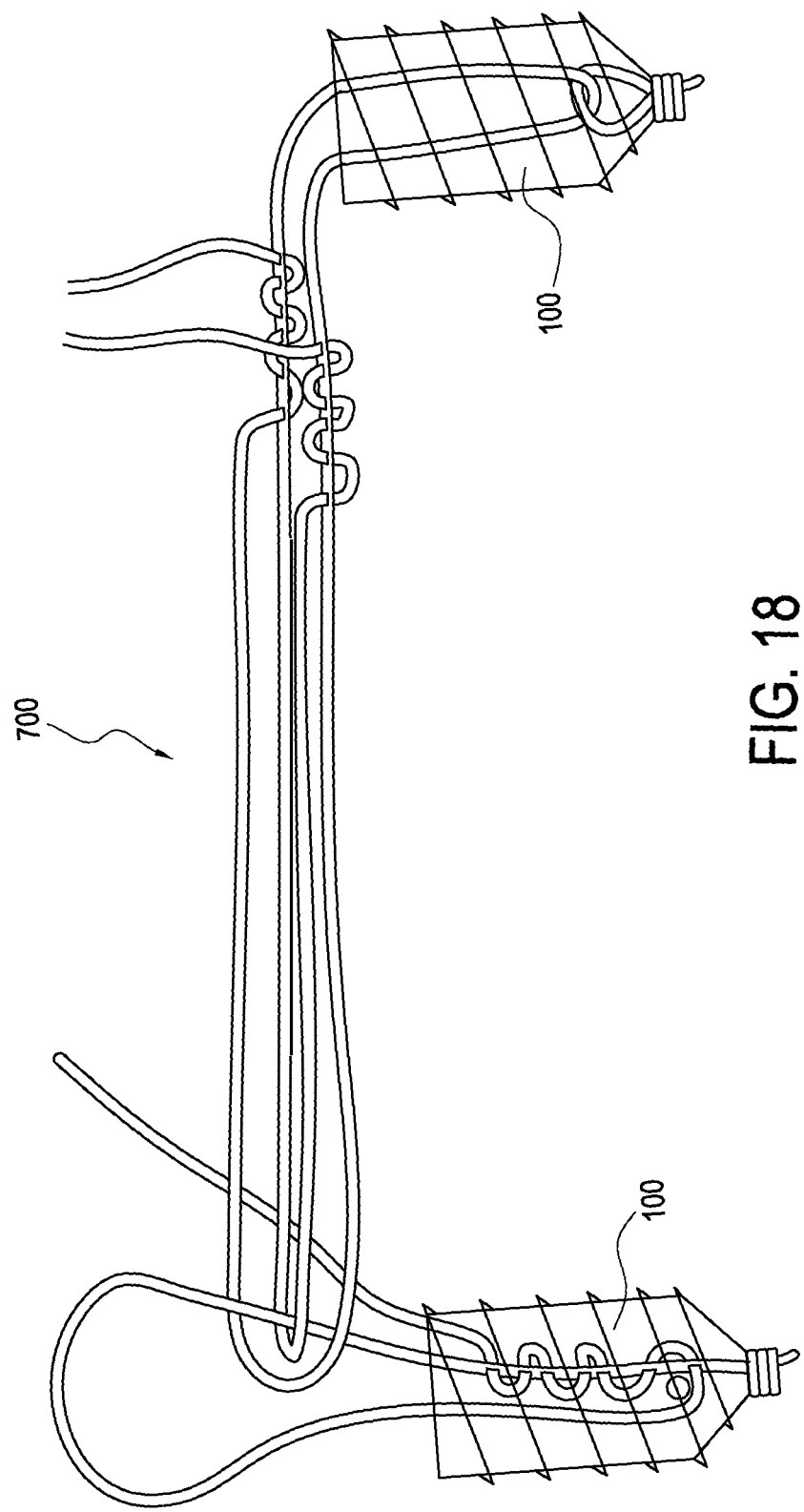

FIGS. 17 and 18 illustrate an adjustable internal brace repair 700 with the constructs of the present disclosure. The anchor assembly is pre-loaded with the adjustable loops and the accordion-style weave regions (locking mechanisms) are formed. The tails are pulled to shrink the loops and tighten the construct. The sutures can be free loose ends evened out by the surgeon, or solid with a mark identifying the center to indicate even lengths. Construct 701 may be any fixation device, for example, an anchor, implant, screw, plate, etc. Construct 701 may be a PushLock® or SwiveLock® anchor as detailed and described in U.S. Pat. Nos. 7,803,173; 7,328,272; and 9,521,999, the disclosures of all of which are incorporated in their entireties herewith.

In FIG. 18, the implant 100 is provided with a shuttle wire in place, to facilitate the passing of suture through the collapsible loops, then shuttled through anchor to form the accordion-weave locking mechanism.

Figure 19:
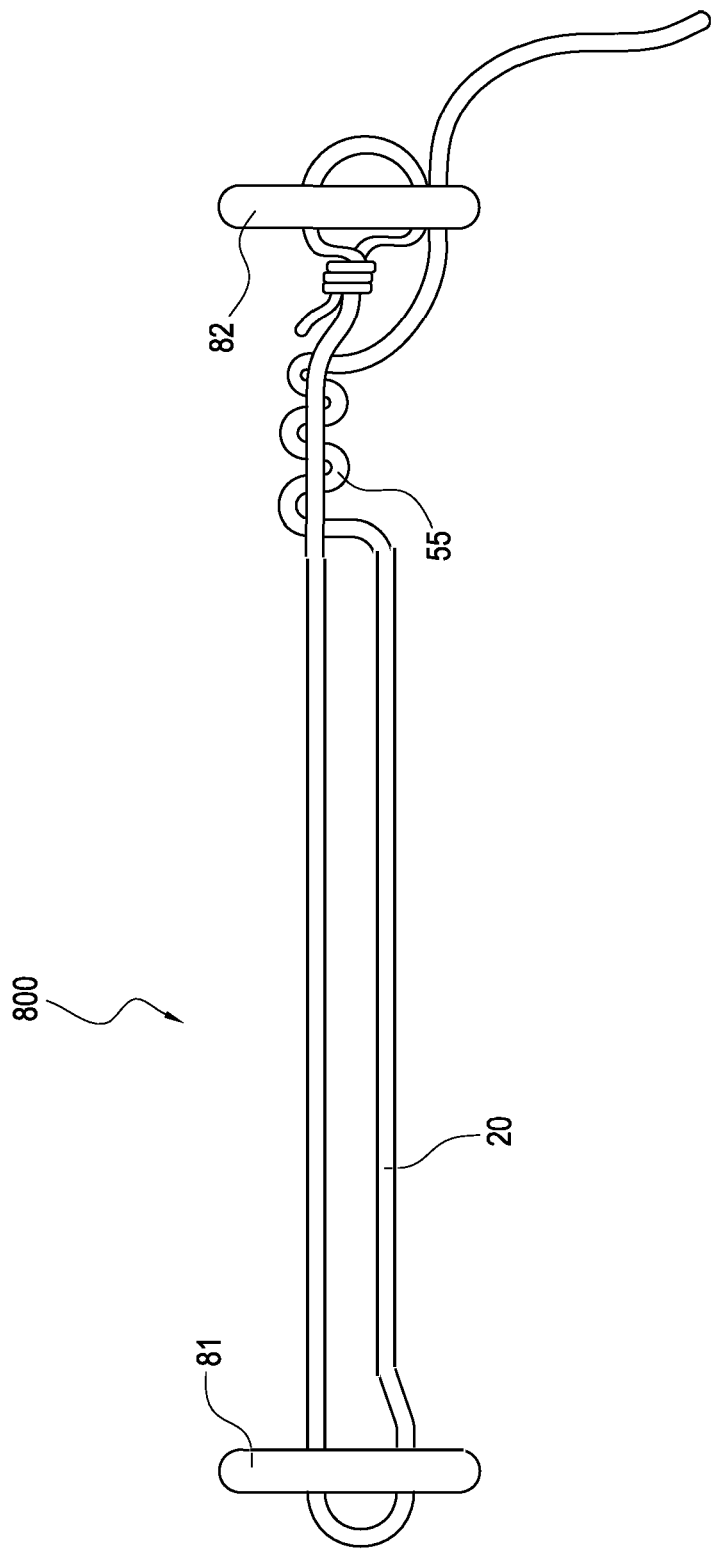

FIG. 19 illustrates another repair 800 which is a self-locking MiniTightRope repair with two fixation devices in the form of two buttons 81, 82 extending between the accordion-weave locking mechanism of the construct of the present disclosure.

Mechanism 99, 99*a*, 199 of the present disclosure may be employed with any fixation device that allows formation of an accordion-style region within or outside the body of the fixation device, with or without the aid of a shuttling device, and allow a flexible coupler (suture tape) and attached suture passing device to form an accordion-style weave region within the body of the fixation device. The fixation devices may be any of swivel and/or screw-in suture anchors and/or push-in suture anchors (such as an Arthrex SwiveLock® anchor, disclosed in U.S. Pat. No. 9,005,246 issued Apr. 14, 2015 or a PushLock® anchor, as disclosed in U.S. Pat. No. 7,329,272 issued Feb. 12, 2008). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others. The fixation devices may be unitary or may be multiple-piece constructs.

Tensionable knotless anchors of the present disclosure may have the designs and configurations of those disclosed in U.S. Pat. No. 9,107,653 issued Aug. 18, 2015 and U.S. Pat. No. 9,855,029 issued Jan. 2, 2018, the disclosures of both of which are incorporated in their entireties herewith. The final accordion-style weave region 55 may be also located outside the anchor body of tensionable anchor 10 but within the bone tunnel or socket. In certain embodiments, the accordion-style weave region 55 may be located outside or inside the anchor body of tensionable anchor 10, and outside or inside the bone tunnel or socket. In certain embodiments, the accordion-style weave region 55 may be located partially outside the anchor body and partially inside the anchor body of tensionable anchor 10, and partially outside the bone tunnel or socket and partially inside the bone tunnel or socket.

The surgical constructs and methods of the present disclosure provide self-locking mechanisms, self-locking tensionable constructs and surgical constructs, as well as methods for tissue repair, for example, attachment of a first tissue to a second tissue, such as soft tissue to bone, with such constructs.

The surgical devices of the present disclosure are knotless TapeTak devices used for the reattachment of soft tissue to bone. The device is comprised of an anchor body on an inserter, one continuous flat/tape flexible coupler fastened to the anchor body at one end, with the other tail run up the insertion device. A shuttle device is pre-loaded, woven through the flat/tape flexible coupling. The free end of the flexible coupling is passed through soft tissue, then fed into the shuttle to create a circumferential loop around the soft tissue. The flexible coupling is woven through itself in an accordion/pleat fashion to create a self-locking mechanism. After flat/tape flexible coupling has been shuttled through itself to form the accordion/pleat weave self-locking mechanism, the free end of the flat/tape flexible coupling is pulled to collapse the loop and compress soft tissue to bone.

Methods of self-locking tissue repairs are also disclosed. In an embodiment, at least one flexible coupler is looped to form a self-locking loop construct (a tensionable self-locking mechanism) with a knotless, continuous, flexible, closed adjustable loop having an adjustable perimeter; an accordion-style weave region; and two terminal ends, one static end and one flexible end. The flexible end is passed through different points spaced apart a length of the flexible coupler and a distance away from the static end, to form a pleat/accordion weave region with a plurality of locking points. The flexible end may be slidably passed through the flexible coupler. The flexible end may be passed through the flexible coupler at different separate points, beginning with a first point and then passing the terminal end through another, second point (at a position adjacent the first point) to form the knotless, continuous, flexible, closed adjustable loop and the pleat/accordion weave. When the flexible end is pulled, the construct shrinks, i.e., the perimeter of the loop decreases. The distance between any of the locking points may also decrease. The tensionable construct allows the user (for example, surgeon) to control the tension of the flexible coupler on first tissue (for example, soft tissue) to be attached to a second tissue (for example, bone) and to lock the construct.

An exemplary method of tissue repair with surgical construct 100 (including fixation device 10, flexible coupler 20 and passing device 40) comprises inter alia the steps of: (i) providing a surgical system 101 comprising a fixation device 10 (for example, anchor) with a flexible coupler 20 (for example, suture tape) fixed to the fixation device 10 (by knot 22, for example) and with a shuttle/pull device 40 (a suture passing instrument) attached to the flexible coupler 20; (ii) inserting the fixation device 10 into bone; (iii) passing the flexible coupler 20 around or through tissue to be fixated (or reattached) to bone, and then through an eyelet/loop 43 of the shuttle/pull device 40; (iv) subsequently, pulling on the shuttle/pull device 40 to allow the flexible coupler 20 to pass through itself and to form an accordion-style weave region 55 within or outside of the body of the fixation device (with the flexible coupler 20 passing multiple times through itself); and (v) pulling on flexible end 23 of flexible coupler 20 to allow the soft tissue to achieve the desired location relative to the bone, and to allow proper tensioning and locking of the final construct.

Another exemplary method of tissue repair with surgical construct 110 (including fixation device 10 and flexible coupler 20) comprises inter alia the steps of: (i) providing a surgical system 101 comprising a fixation device 10 (for example, anchor) with a flexible coupler 20 (for example, suture tape) with two free ends extending through a body of the fixation device and attached to the fixation device through a flexible eyelet or loop; (ii) forming an accordion-style weave region 55 within or outside of the body of the fixation device (with the flexible coupler 20 passing multiple times through itself); (iii) joining the two free ends together to form a single end; (iv) passing the single end through or around tissue to be attached; and (v) removing the single end to form again two free ends of the flexible coupler. The free ends may then be employed to allow the soft tissue to achieve the desired location relative to the bone, and to allow proper tensioning and locking of the final construct. A plurality of flexible couplers may be loaded onto the fixation device (for example, each being looped through and passed through a flexible eyelet or small loop at the distal end of the fixation device) and their free ends may be joined together in any combination to form one or more single ends (which in turn may be joined together multiple times to form a single end).

Fixation device 10 may be an anchor formed of metal, biocompatible plastic such as PEEK or a bioabsorbable PLLA material or a biocomposite material. The anchors may be provided with a socket at the distal end (such as socket 19 of the anchor 10) configured to securely engage a tip of a driver. The socket of the anchor may have any shape adapted to receive a driver tip for pushing the anchors, for example, tap-in or screw-in style anchors. Tensionable knotless anchor 10 may be made of one or more pieces, or may be provided as an integrated device.

The flexible coupler 20 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

The flexible coupler 20 may include any flexible materials or strands such as suture or tape, for example, multifilament, braided, knitted, woven suture, or including fibers of ultra-high molecular weight polyethylene (UHMWPE). The flexible couplers may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Surgical self-locking constructs can be used with any type of flexible material or suture known in the art. If suture tape is employed, the tape may have sections with different tapers (for example, 3 or 4 sections of gradual tapers or gradual widths) to facilitate easy formation of the accordion-style weave regions 55.

The flexible coupler 20 may be also formed of a stiff material, or combination of stiff and flexible materials, particularly for the regions of the couplers that are weaved through the body of the coupler and depending on whether they are employed with additional fixation devices. In addition, flexible couplers may be also coated and/or provided in different colors for easy manipulation during the surgical procedure. The knotless constructs and self-locking soft anchors of the present disclosure can be used with any type of flexible material or suture that may be weaved or passed through itself.

If desired, flexible coupler 20 may be coated, impregnated, or otherwise stiffened with a material such as plastic, for example.

The flexible coupler 20 and/or passing device 40 may be also provided with tinted tracing strands, or otherwise contrast visually with the sheath of the construct, which remains a plain, solid color, or displays a different tracing pattern, for example. Various structural elements of surgical construct 100, 110 may be visually coded, making identification and handling of the suture legs simpler. Easy identification of suture in situ is advantageous in surgical procedures, particularly during arthroscopic surgeries, endoscopic and laparoscopic procedures.

The present disclosure provides a method of tissue repair, comprising the steps of: installing a fixation device in bone, the fixation device comprising a body, a flexible coupler with two free ends extending through at least a portion of the body and attached to the fixation device by being secured to a flexible eyelet of the fixation device, forming a first accordion-style region in the flexible coupler and a first knotless closed loop having an adjustable perimeter, with one of the two free ends; and joining together the two free ends to form a single end and a second forming a knotless closed loop having an adjustable perimeter. The method further comprises the steps of: passing the single end of the flexible coupler around or through soft tissue to be fixated; and removing the single end to form again two free ends. The flexible eyelet is located at a distal end of the fixation device.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A method of tissue repair, comprising:
    installing a first fixation device in bone, the first fixation device comprising a body, at least one flexible coupler with two ends, the at least one flexible coupler extending through at least a portion of the body and at least one shuttling device passing through the at least one flexible coupler to form at least one accordion-style region in the at least one flexible coupler; and
    attaching one end of the at least one flexible coupler to a second fixation device.

2. The method of claim 1, further comprising attaching other end of the at least one flexible coupler to a third fixation device.

3. The method of claim 1, further comprising:
    passing one end of the at least one flexible coupler around or through soft tissue to be fixated, and then attaching the one end of the at least one flexible coupler to the shuttling device;
    pulling the one end of the at least one flexible coupler through the first accordion-style region, thereby forming a first knotless closed loop having an adjustable perimeter and a second accordion-style region; and
    attaching the other end of the at least one flexible coupler to the second fixation device.

4. The method of claim 1, further comprising connecting the second or third fixation device to at least another fixation device.

5. The method of claim 1, further comprising connecting the second and third fixation device to at least another fixation device.

6. The method of claim 1, wherein the first fixation device comprises two flexible couplers, each flexible couplers having two ends, and two shuttling devices, each shuttling device passing through one flexible coupler to each form an accordion-style region and a knotless closed loop with an adjustable perimeter.

7. The method of claim 6, further comprising connecting at least one end of each of the two flexible couplers to at least two different fixation devices.

8. The method of claim 1, wherein the tissue repair is a tension bridge repair for rotator cuff.

9. A method of tissue repair, comprising:
    installing a plurality of fixation devices in bone, each of the plurality of fixation device comprising a body, a flexible coupler with two ends, the flexible coupler extending through at least a portion of the body and a corresponding shuttling device passing through the flexible coupler to form a first accordion-style region in the flexible coupler;
    after installing the plurality of fixation devices in bone, passing one end of each of the flexible couplers around or through soft tissue to be fixated, and then attaching the one end of each of the flexible couplers to the corresponding shuttling device;
    pulling the one end of each of the flexible couplers through the first accordion-style region, thereby forming a first knotless closed loop having an adjustable perimeter and a second accordion-style region; and
    attaching the other end of each of the flexible couplers to additional fixation devices.

10. The method of claim 9, further comprising:
    pre-loading each of the plurality of fixation devices with a corresponding flexible coupler and shuttling device;
    securing each of the plurality of fixation devices to a driver by tying the flexible coupler and the shuttling device to the driver;
    inserting each of the plurality of the fixation devices into a hole in the bone;
    passing each of the flexible couplers through or around the soft tissue to be fixated;

subsequently, threading each of the flexible couplers through an eyelet of the corresponding shuttling device; and pulling on the shuttling device such that the flexible coupler is passed numerous times through itself to create the first knotless closed loop and the second accordion-style region, for approximating the soft tissue to the bone.

11. A method of tissue repair, comprising the steps of:

installing a first fixation device in bone, the first fixation device comprising a body, a first flexible coupler with two ends, the first flexible coupler extending through at least a portion of the body and a first shuttling device passing through the first flexible coupler to form a first accordion-style region in the first flexible coupler;

after installing the first fixation device in bone, passing one end of the first flexible coupler around or through soft tissue to be fixated, and then attaching the one end of the first flexible coupler to the first shuttling device;

pulling the one end of the first flexible coupler through the first accordion-style region, thereby forming a first knotless closed loop having an adjustable perimeter and a second accordion-style region; and connecting the first fixation device to one or more fixation devices, by attaching the one end of the first flexible coupler of the first fixation device to a second shuttling device attached to a second flexible coupler of the one or more fixation devices, and pulling the second shuttling device out of the one or more fixation devices to create a second knotless closed loop and a third accordion-style region.

12. The method of claim 11, wherein the tissue repair comprises four connected fixation devices.

13. The method of claim 11, further comprising pulling on the first shuttling device such that the first flexible coupler is passed numerous times through itself to create the first knotless closed loop and the second accordion-style region, for approximating the soft tissue to the bone.

* * * * *